(12) United States Patent
Narasimhan et al.

(10) Patent No.: US 11,547,663 B2
(45) Date of Patent: *Jan. 10, 2023

(54) UNIT AEROSOL DOSES FOR ANTICOAGULATION

(71) Applicants: InCarda Therapeutics, Inc., Palo Alto, CA (US); The Regents of the University of California, Oakland, CA (US)

(72) Inventors: Rangachari Narasimhan, Saratoga, CA (US); Gregory Marcus, San Francisco, CA (US)

(73) Assignees: InCarda Therapeutics, Inc., Palo Alto, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/890,264

(22) Filed: Jun. 2, 2020

(65) Prior Publication Data

US 2020/0360280 A1 Nov. 19, 2020

Related U.S. Application Data

(63) Continuation of application No. 15/317,282, filed as application No. PCT/US2016/014126 on Jan. 20, 2016, now Pat. No. 10,668,015.

(Continued)

(51) Int. Cl.
*A61K 9/00* (2006.01)
*A61K 31/4709* (2006.01)
(Continued)

(52) U.S. Cl.
CPC ............ *A61K 9/0078* (2013.01); *A61K 9/008* (2013.01); *A61K 9/0075* (2013.01); *A61K 31/37* (2013.01);
(Continued)

(58) Field of Classification Search
None
See application file for complete search history.

(56) References Cited

U.S. PATENT DOCUMENTS 5,389,618 A 2/1995 Debrie
6,063,407 A * 5/2000 Zapol ..................... A61P 9/10
424/718

(Continued)

FOREIGN PATENT DOCUMENTS

IT 1103110 10/1985
WO 2004073747 A1 9/2004
(Continued)

OTHER PUBLICATIONS

Pieter R Tuinman, Barry Dixon, Marcel Levi, Nicole P Juffermans and Marcus J Schultz. "Nebulized anticoagulants for acute lung injury—a systematic review of preclinical and clinical investigations." Critical Care, 16:R70, 2012, pp. 1-10. (Year: 2012).*

(Continued)

*Primary Examiner* — Isaac Shomer
(74) *Attorney, Agent, or Firm* — Sean D. Solberg; Tina G. Yin Sowatzke

(57) ABSTRACT

Disclosed herein are methods for prophylactic treatment of acute coronary syndrome (ACS) comprising administering, by inhalation, an effective amount of a pharmaceutical composition comprising at least one anticoagulant or antiplatelet agent to a subject in need thereof, wherein the anticoagulant or antiplatelet agent first enters the heart via the left atrium.

18 Claims, 3 Drawing Sheets

Related U.S. Application Data

(60) Provisional application No. 62/105,644, filed on Jan. 20, 2015.

(51) Int. Cl.

| | | |
|---|---|---|
| *A61K 31/616* | (2006.01) | |
| *A61P 7/02* | (2006.01) | |
| *A61K 31/727* | (2006.01) | |
| *A61K 31/4365* | (2006.01) | |
| *A61K 31/37* | (2006.01) | |
| *A61K 31/4465* | (2006.01) | |
| *A61K 38/12* | (2006.01) | |

(52) U.S. Cl.
CPC ...... *A61K 31/4365* (2013.01); *A61K 31/4465* (2013.01); *A61K 31/4709* (2013.01); *A61K 31/616* (2013.01); *A61K 31/727* (2013.01); *A61K 38/12* (2013.01); *A61K 9/007* (2013.01); *A61P 7/02* (2018.01)

(56) References Cited

U.S. PATENT DOCUMENTS

| 10,668,015 | B2* | 6/2020 | Narasimhan | A61K 31/727 |
|---|---|---|---|---|
| 2006/0014698 | A1* | 1/2006 | O'Connor | A61K 9/0078 514/1.7 |
| 2007/0238674 | A1 | 10/2007 | Veltri et al. | |
| 2008/0293633 | A1* | 11/2008 | Bisgaier | A61K 9/127 514/1.1 |
| 2010/0016356 | A1* | 1/2010 | Song | A61K 31/4709 514/314 |
| 2012/0003318 | A1* | 1/2012 | Schuler | A61K 31/445 424/489 |
| 2013/0199527 | A1* | 8/2013 | Smutney | A61M 15/0048 128/203.15 |

FOREIGN PATENT DOCUMENTS

| WO | 2011038047 A1 | 3/2011 |
|---|---|---|
| WO | 2014012236 A1 | 1/2014 |

OTHER PUBLICATIONS

Ezra A. Amsterdam et al. "2014 AHA/ACC Guideline for the Management of Patients With Non-ST-Elevation Acute Coronary Syndromes." Circulation, vol. 130, 2014, pp. e344-e426. (Year: 2014).*

University of Minnesota. Physiology Tutorial, www.vhlab.umn.edu/atlas/physiology-tutorial/the-human-heart.shtml accessed Aug. 12, 2020, pp. 1-2. (Year: 2020).*

Ignacio Cruz-Gonzalez, Rosana Lopez-Jimenez, Angel Ferez-Rivera & Bryan P Yan. "Pharmacokinetic evaluation or argatroban for the treatment of acute coronary syndrome." Expert Opinion on Drug Metabolism and Toxicity, vol. 8(11), 2012, pp. 1483-1493. (Year: 2012).*

John S. Patton and Peter R. Byron. "Inhaling medicines: delivering drugs to the body through the lungs." Nature Reviews Drug Discovery, vol. 6, Jan. 2007, pp. 67-74. (Year: 2007).*

Philippe Meurin, Jean Yves Tabet, Hélène Weber, Nathalie Renaud, Ahmed Ben Driss. "Low-Molecular-Weight Heparin as a Bridging Anticoagulant Early After Mechanical Heart Valve Replacement." Circulation, vol. 113, 2006, pp. 564-569. (Year: 2006).*

Catherine J. Lee & Jack E. Ansell. "Direct thrombin inhibitors." British Journal of Clinical Pharmacology, vol. 72:4, 2011, pp. 581-592. (Year: 2011).*

United States Court of Appeals of the Federal Circuit. "In re Cyclobenzaprine Hydrochloride Extended-Release Capsule Patent Litigation." Appeal # 2011-1399, -1409, Decided Apr. 16, 2012, pp. 1-48. (Year: 2012).*

Ninell P. Mortensen and Anthony J. Hickey. "Targeting Inhaled Therapy beyond the Lungs." Respiration, vol. 88, 2014, pp. 353-364. (Year: 2014).*

Johannes D. de Boer et al. "Effect of the oral thrombin inhibitor dabigatran on allergic lung inflammation induced by repeated house dust mite administration in mice." American Journal of Physiology Lung Cell and Molecular Physiology, vol. 309, 2015, pp. L768-L775. (Year: 2015).*

Brosa, M. et al., "Cost-effectiveness analysis of enoxaparin versus unfractionated heparin in the secondary prevention of acute coronary syndrome", Jan. 1, 2002, pp. pp. 979-987, vol. vol. 20, No. No. 14, Publisher: Pharmacoeconomics, ADIS International, Published in: Auckland, NZ.

Lotto, A. et al., "Heparin and secondary prevention of acute myocardial infarction", Jan. 1, 1990, pp. pp. 132-141, vol. vol. 20, No. SU PPL, Publisher: HAEMOSTASIS, Published in: Basel, CH.

Molino et al., "Results with longterm aerosol administiation of heparin in 86 cardiovascular patients with thrombophilic tendencies / Considerazioni sull'uso dell'Eparina long-term nei cardiovasculopatici", Jan. 1, 1973, pp. pp. 553-557, vol. vol. 21, No. No. 7-8, Publisher: Minerva Cardioangiolo, Edizioni Minerva Medica, Published in: Torino, IT.

Rawat et al., "Inhalable large porous microspheres of low molecular weight heparin: In vitro and in vivo evaluation", Jun. 24, 2008, pp. pp. 224-232, vol. vol. 128, No. No. 3, Publisher: Journal of Controlled Release, Published in: Amsterdam, NL.

Willentin et al., "Oral ximelagatran for secondary prophylaxis after myocardial infarction: the ESTEEM randomised controlled trial", Sep. 3, 2003, pp. pp. 789-797, vol. vol. 362, No. No. 9386, Publisher: Lancet, Elsevier, Published in: Amsterdam, NL.

"Cardiology Femoral Sheath Removal Protocol", Sep. 10, 2003, Publisher: Vanderbilt University Medical Center.

Matsuyama et al., "Difficulty in the Management of Anticoagulation with Argatroban during off-pump Coronary artery Bypass Grafting", "Journal of Cardiology Cases", Feb. 21, 2013, Publisher: Elsevier Ltf.

Jennifer A. Niederstadt, "Frequency and Timing of Activated Clotting Time Levels for Sheath Removal", Nov. 29, 2003, pp. 34-38, vol. 19, No. 1, Publisher: Lippincott Williams $ Williams, Inc.

University of Rochester Medical Center, "Activated Coagulation Time" downloaded Dec. 16, 2019.

\* cited by examiner

UNIT AEROSOL DOSES FOR ANTICOAGULATION

CROSS-REFERENCE

This application is a continuation of U.S. application Ser. No. 15/317,282, filed Dec. 8, 2016 and entitled "Unit Aerosol Doses For Anticoagulation," which was filed under 35 U.S.C. § 371 and claims priority to International PCT Application No. PCT/US16/14126, filed on Jan. 20, 2016 and entitled "Unit Aerosol Doses For Anticoagulation,", which claims benefit of U.S. Provisional Application No. 62/105,644 filed on Jan. 20, 2015 and entitled "Unit Aerosol Doses For Anticoagulation," under 35 U.S.C. § 365, all of which are hereby incorporated herein by reference in their entireties.

BACKGROUND OF THE INVENTION

There are several treatment strategies employed to treat acute coronary syndrome (ACS). One is the administration of antithrombotic drugs that prevent and/or dissolve blood clots. Antithrombotics include anticoagulants, antiplatelet agents, thrombolytics and statins. All of these are either used individually or in combination primarily in a prophylactic setting. While some of the drugs are available as oral or sub-cutaneous injections, a majority of these are administered as intra-venous (IV) injections, requiring a hospital or physician office environment is required for drug administration. The need to provide these via an IV route has resulted in some of these drugs like antiplatelet inhibitors and thrombolytics being used only in acute settings, for example, primarily before a Percutaneous Transluminal Coronary Angioplasty (PTCA) or Percutaneous Coronary Intervention (PCI) procedures and/or Coronary Arterial Bypass Graft (CABG) surgery.

There are several treatment strategies employed to treat patients who have undergone mitral and/or other heart valve replacements. One is the administration of antithrombotic drugs that prevent and/or dissolve blood clots. Antithrombotics include anticoagulants, antiplatelet agents, thrombolytics and statins. All of these are either used individually or in combination primarily in a prophylactic setting. While some of the drugs are available as oral or sub-cutaneous injections, a majority of these are administered as intra-venous (IV) injections, requiring a hospital or physician office environment is required for drug administration. The need to provide these via an IV route has resulted in some of these drugs like antiplatelet inhibitors and thrombolytics being used only in acute settings, for example, primarily after a heart valve replacement.

There are several treatment strategies employed to treat acute coronary syndrome (ACS) associated with blockage in the micro capillaries that provide blood to the myocardium. These patients do not qualify for Percutaneous Transluminal Coronary Angioplasty (PTCA) or Percutaneous Coronary Intervention (PCI) procedures and/or Coronary Arterial Bypass Graft (CABG) surgery. These patients are therefore managed by one or more strategies employing antithrombotics and anticoagulants. One is the administration of antithrombotic drugs that prevent and/or dissolve blood clots. Antithrombotics include anticoagulants, antiplatelet agents, thrombolytics and statins. All of these are either used individually or in combination primarily in a prophylactic setting. While some of the drugs are available as oral or sub-cutaneous injections, a majority of these are administered as intra-venous (IV) injections, requiring a hospital or physician office environment is required for drug administration. The need to provide these via an IV route has resulted in some of these drugs like antiplatelet inhibitors and thrombolytics being used only in acute hospital settings.

There are several treatment strategies employed to treat patients who have undergone heart transplant. One is the administration of antithrombotic drugs that prevent and/or dissolve blood clots. Antithrombotics include anticoagulants, antiplatelet agents, thrombolytics and statins. All of these are either used individually or in combination primarily in a prophylactic setting. While some of the drugs are available as oral or sub-cutaneous injections, a majority of these are administered as intra-venous (IV) injections, requiring a hospital or physician office environment is required for drug administration. The need to provide these via an IV route has resulted in some of these drugs like antiplatelet inhibitors and thrombolytics being used only in acute settings, for example, primarily after a heart transplant.

The drug delivery technology limitations have prevented the use of these classes in a chronic setting. The development of antiplatelet inhibitors as oral pills failed clinical testing in humans. The ability to achieve a differentiated PK is important to reducing adverse events that are dose and extent related. Anticoagulants administered via subcutaneous (SC) and oral routes present a high steady state concentration several magnitudes more than the required concentration in the heart as they have to compensate for the routes of delivery.

It is an object of the present invention to provide a non-invasive antiplatelet inhibitor therapy as a prophylactic for ischemic heart conditions associated with the presence of unstable angina (UA), angina, non-ST elevated myocardial infarction (NSTEMI), ST elevated myocardial infarction (STEMI), atrial fibrillation (AF), etc.

It is a further object of the present invention to deliver these drugs directly to the heart and its associated tissues, providing maximum and quick benefit to the regions of the heart where this medication is needed to prevent platelet formation and hence ischemic conditions from recurring.

It is another object of the invention to reduce the exposure of the drug to the rest of the body, thereby reducing associated adverse events such as bleeding.

SUMMARY OF THE INVENTION

Disclosed herein are methods for prophylactic treatment (e.g. antithrombotic treatment) of acute coronary syndrome (ACS) comprising administering, by inhalation, an effective amount of a pharmaceutical composition comprising at least one anticoagulant or antiplatelet agent to a subject in need thereof, wherein the anticoagulant or antiplatelet agent first enters the heart via the left atrium. In some embodiments, the methods are used in heart valve replacements patients and/or in heart transplant patients.

In some embodiments, the subject is a human patient. For example, the patient is suffering from at least one condition selected from the group consisting of stable angina, unstable angina, myocardial infarction, valvular heart disease, stroke, and atrial fibrillation. In some embodiments, the patient has known blockages in the capillaries that supply blood to the myocardium and cannot be treated by coronary arterial bypass graft (CABG). In some embodiments, the patient has undergone heart transplant or a valve replacement in the heart. In some embodiments, the method can further comprise treating the patient with coronary artery bypass (CABG) surgery or angioplasty. In some embodiments, the acute coronary syndrome comprises ischemic events, clotting, angina, myocardial infarction, or any combination thereof.

In another aspect, about 10% to 80% of the administered pharmaceutical composition reaches the left atrium. In some embodiments, the amount of the pharmaceutical composition peaks in the left atrium at a time ranging from 30 seconds to 180 minutes, 30 seconds to 120 minutes, 30 seconds to 90 minutes, 30 seconds to 60 minutes, or 30 seconds to 30 minutes after initiating the administration. In some embodiments, the amount of the pharmaceutical composition peaks in the left atrium in less than about 20 minutes, such as less than about 10 seconds, 20 seconds, 30 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. In some embodiments, the amount of the pharmaceutical composition peaks in the left atrium in about 10 seconds to 180 minutes, such as about 10-20 seconds, 10-30 seconds, 10 seconds to 1 minute, 10 seconds to 2 minutes, 10 seconds to 3 minutes, 10 seconds to 5 minutes, 10 seconds to 10 minutes, 10 seconds to 20 minutes, 10 seconds to 30 minutes, 10 seconds to 60 minutes, 10 seconds to 90 minutes, 10 seconds to 120 minutes, 10 seconds to 180 minutes, 30 seconds to 1 minute, 30 seconds to 2 minutes, 30 seconds to 3 minutes, 30 seconds to 5 minutes, 30 seconds to 10 minutes, 30 seconds to 20 minutes, 30 seconds to 30 minutes, 30 seconds to 60 minutes, 30 seconds to 90 minutes, 30 seconds to 120 minutes, 30 seconds to 180 minutes, 1-2 minutes, 1-5 minutes, 1-10 minutes, 1-20 minutes, 1-30 minutes, 1-60 minutes, 1-90 minutes, 1-120 minutes, 1-180 minutes, 3-5 minutes, 3-10 minutes, 3-20 minutes, 3-30 minutes, 3-60 minutes, 3-90 minutes, 3-120 minutes, 3-180 minutes, 5-10 minutes, 5-20 minutes, 5-30 minutes, 5-60 minutes, 5-90 minutes, 5-120 minutes, 5-180 minutes, 10-20 minutes, 10-30 minutes, 10-60 minutes, 10-90 minutes, 10-120 minutes, 10-180 minutes, 20-30 minutes, 20-60 minutes, 20-90 minutes, 20-120 minutes, 20-180 minutes, 30-60 minutes, 30-90 minutes, 30-120 minutes, 30-180 minutes, 60-90 minutes, 60-120 minutes, 60-180 minutes, 90-120 minutes, 90-180 minutes, or 120-180 minutes. In some embodiments, about 5% to 99%, such as about 5%-99%, 10%-99%, 15%-99%, 20%-99%, 30%-99%, 40%-99%, 50%-99%, 60%-99%, 70%-99%, 80%-99%, 90%-99%, 5%-90%, 10%-90%, 15%-90%, 20%-90%, 30%-90%, 40%-90%, 50%-90%, 60%-90%, 70%-90%, 80%-90%, 5%-80%, 10%-80%, 15%-80%, 20%-80%, 30%-80%, 40%-80%, 50%-80%, 60%-80%, 70%-80%, 5%-70%, 10%-70%, 15%-70%, 20%-70%, 30%-70%, 40%-70%, 50%-70%, 60%-70%, 5%-60%, 10%-60%, 15%-60%, 20%-60%, 30%-60%, 40%-60%, 50%-60%, 5%-50%, 10%-50%, 15%-50%, 20%-50%, 30%-50%, 40%-50%, 5%-40%, 10%-40%, 15%-40%, 20%-40%, 30%-40%, 5%-30%, 10%-30%, 15%-30%, 20%-30%, 5%-20%, 10%-20%, 15-20%, or 5%-10% of the administered pharmaceutical composition reaches the coronary arteries that supply blood to the myocardium. In some embodiments, about 5% to 20% of the administered pharmaceutical composition reaches the coronary arteries that supply blood to the myocardium. In some embodiments, the pharmaceutical composition has a dosage from 0.05 mg to 150 mg, 0.5 mg to 100 mg, or 1 mg to 50 mg. In some embodiments, the pharmaceutical composition has a dosage of 0.05 mg to 150 mg, for example, about 0.05-150, 0.05-130, 0.05-110, 0.05-90, 0.05-70, 0.05-50, 0.05-30, 0.05-10, 0.05-5, 0.05-1, 0.05-0.5, 0.05-0.1, 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 mg. In some embodiments, the effective amount of the pharmaceutical composition produces a ratio of factor-Xa to factor-XIIa activity in the left atrium peaking at a range from 3 to 21. In some embodiments, the effective amount of the pharmaceutical composition produces a ratio of factor-Xa to factor-IIa activity in the left atrium of at least about 0.05, such as at least about 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 20, 30, 40, or 50.

In some embodiments, the pharmaceutical composition is administered by a condensation aerosol, a liquid inhalation system, or a nebulizer. In some embodiments, the nebulizer is a vibrating mesh nebulizer or a jet nebulizer. In some embodiments, the pharmaceutical composition is administered via an active dry powder inhaler, a passive dry powder inhaler, or a metered dose inhaler. In some embodiments, the method further comprising forming aerosol, dry power, or nebulized droplets having a mass median aerodynamic diameter of less than about 100 μm, for example, less than about 1, 2, 3, 4, 5, 6, 7, 8, 9, 10, 20, 30, 40, 50, 60, 70, 80, 90, or 100 μm.

In some embodiments, the pharmaceutical composition comprises at least one anticoagulant. In some embodiments, the anticoagulant is selected from the group consisting of coumarin, heparin, low-molecular-weight heparin (LMWH), synthetic pentasaccharide inhibitor of factor Xa, direct factor Xa inhibitor, and direct thrombin inhibitor. In some embodiments, the coumarin is vitamin K antagonist. In some embodiments, the coumarin comprises warfarin, acenocoumarol, phenprocoumon, atromentin, or phenindione.

In some embodiments, the anticoagulant is heparin. In some embodiments, the heparin has an average molecular weight of about 5 to 100 kDa, for example, about 5-10 kDa, about 5-20 kDa, about 5-30 kDa, about 5-40 kDa, about 5-50 kDa, about 5-60 kDa, about 5-70 kDa, about 5-80 kDa, about 5-90 kDa, about 5-100 kDa, about 10-20 kDa, about 10-40 kDa, about 10-60 kDa, about 10-80 kDa, about 10-100 kDa, about 20-40 kDa, about 20-60 kDa, about 20-80 kDa, about 20-100 kDa, about 40-60 kDa, about 40-80 kDa, about 40-100 kDa, about 60-80 kDa, about 60-100 kDa, or about 80-100 kDa.

In some embodiments, the anticoagulant is LMWH. In some embodiments, the LMWH has an average molecular weight of less than about 15 kDa, for example, less than about 0.1 k Da, 0.5 kDa, 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, or 15 kDa. In some embodiments, the LMWH has an average molecular weight of less than about 8 kDa. In some embodiments, at least about 50%, for example, at least about 50%, 55%, 60%, 65%, 70%, 75%, 80%, 85%, 90%, or 95% of all chains of the LMWH have a molecular weight less than 10 kDa. In some embodiments, at least 60% of all chains of the LMWH have a molecular weight less than 10 kDa.

In some embodiments, the LMWH is selected from the group consisting of ardeparin, certoparin, enoxaparin, pamaparin, tinzaparin, dalteparin, reviparin, and nadroparin.

In some embodiments, the at least one anticoagulant or antiplatelet agent, such as heparin or LMWH, has a potency of greater than about 10 units/mg of anti-factor Xa activity. In some embodiments, the at least one anticoagulant or antiplatelet agent, such as heparin or LMWH, has a potency of greater than about 10 units/mg, for example, greater than about 10 units/mg, 15 units/mg, 20 units/mg, 25 units/mg, 30 units/mg, 35 units/mg, 40 units/mg, 45 units/mg, 50 units/mg, 60 units/mg, 70 units/mg, 80 units/mg, 90 units/mg, or 100 units/mg of anti-factor Xa activity. In some embodiments, the potency of anti-factor Xa activity can be measured using an anti-factor Xa assay (e.g., a chromogenic assay).

In some embodiments, the anticoagulant is a synthetic pentasaccharide inhibitors of factor Xa. In one example, the synthetic pentasaccharide inhibitor of factor Xa is fondaparinux or idraparinux.

In some embodiments, the anticoagulant is a direct factor Xa inhibitor. In some embodiments, the direct factor Xa inhibitor is selected from the group consisting of rivaroxaban, apixaban, edoxaban, betrixaban, darexaban, TAK-442, eribaxaban, and otamixaban.

In some embodiments, the anticoagulant is a direct thrombin inhibitor (DTI). In some embodiments, the DTI is bivalent DTI, univalent DTI, or allosteric inhibitor. In some embodiments, the bivalent DTI is selected from the group consisting of hirudin, bivalirudin, lepirudin, and desirudin. In some embodiments, the univalent DTI is selected from the group consisting of argatroban, melagatran, ximelagatran, and dabigatran. In some embodiments, the allosteric inhibitor is selected from the group consisting of DNA aptamers, benzofuran dimers, benzofuran trimers, and polymeric lignins. For example, the allosteric inhibitor can be sulfated β-O4 lignin (SbO4L).

In some other embodiments, the anticoagulant is batroxobin or hementin.

In some embodiments, the pharmaceutical composition comprises at least one antiplatelet agent. In some embodiments, the antiplatelet agent is selected from the group consisting of COX inhibitor, adenosine diphosphate (ADP) receptor inhibitor, phosphodiesterase inhibitor, Glycoprotein lib/IIIa inhibitor, adenosine reuptake inhibitor, and thromboxane inhibitor.

In some embodiments, the antiplatelet agent is a COX inhibitor. For example, the COX inhibitor is aspirin or triflusal.

In some embodiments, the antiplatelet agent is an adenosine diphosphate (ADP) receptor inhibitor. In some embodiments, the adenosine diphosphate (ADP) receptor inhibitor is selected from the group consisting of clopidogrel, prasugrel, ticlopidine, ticagrelor, cangrelor, and elinogrel.

In some embodiments, the antiplatelet agent is a phosphodiesterase inhibitor. In some embodiments, the phosphodiesterase inhibitor is vorapaxar or cilostazol.

In some embodiments, the antiplatelet agent is a glycoprotein lib/IIIa inhibitor. In some embodiments, the glycoprotein lib/IIIa inhibitor is selected from the group consisting of abciximab, eptifibatide, tirofiban, roxifiban, and orbofiban.

In some embodiments, the antiplatelet agent is an adenosine reuptake inhibitor. In some embodiments, the adenosine reuptake inhibitor is selected from the group consisting of Acadesine, Acetate, Barbiturates, Benzodiazepines, Calcium channel blockers, Carbamazepine, Carisoprodol, Cilostazol, Cyclobenzaprine, Dilazep, Dipyridamole (Persantine), Estradiol, Ethanol, Flumazenil, Hexobendine, Hydroxyzine, Indomethacin, Inosine, KF24345, Meprobamate, Nitrobenzylthioguanosine, Nitrobenzylthioinosine, Papaverine, Pentoxifylline, Phenothiazines, Phenytoin, Progesterone, Propentofylline, Propofol, Puromycin, R7523 I, RE 102 BS, Soluflazine, Toyocamycin, Tracazolate, and Tricyclic antidepressants.

In some embodiments, the antiplatelet agent is a thromboxane inhibitor. In some embodiments, the thromboxane inhibitor is terutroban or picotamide.

In some embodiments, the pharmaceutical composition is self-administered by the subject. In some embodiments, the pharmaceutical composition is administered in 1 to 10 inhalations, such as 1-3, 1-4, 1-5, 1-6, or 1-10 inhalations. For example, the pharmaceutical composition can be administered in 1 to 10 inhalations.

In some embodiments, the patient reaches an anticoagulated state in less than about 10 hours, for example, less than about 10 hours, 9 hours, 8 hours, 7 hours, 6 hours, 5 hours, 4 hours, 3 hours, 2 hours, 1 hour, 50 minutes, 40 minutes, 30 minutes, 20 minutes, 10 minutes, 5 minutes, 4 minutes, 3 minutes, 2 minutes, or 1 minute after initiating the administration of the pharmaceutical composition. In one example, the patient reaches an anticoagulated state in less than 30 minutes after initiating the administration of the pharmaceutical composition.

In some embodiments, the patient returns from an anticoagulated state to a normal coagulation state in about 1 hour to 10 hours, for example, in about 1-3, 1-4, 1-5, 1-6, 1-7, 1-8, 1-9, 1-10, 2-5, 2-6, 2-7, 2-8, 2-9, 2-10, 5-6, 5-7, 5-8, 5-9, or 5-10 hours after initiating the administration of the pharmaceutical composition. In one example, the patient returns from an anticoagulated state to a normal coagulation state in 1 hour to 8 hours after initiating the administration of the pharmaceutical composition.

In some embodiments, the patient is administered a dosage (e.g., periodic dosage) of 0.05 mg to 150 mg, for example, about 0.05-150, 0.05-130, 0.05-110, 0.05-90, 0.05-70, 0.05-50, 0.05-30, 0.05-10, 0.05-5, 0.05-1, 0.05-0.5, 0.05-0.1, 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 mg of the at least one anticoagulant or antiplatelet agent. In some embodiments, the dosage (e.g., periodic dosage) is administered twice daily, daily, every other day, weekly, or monthly.

In one aspect, the patient is suffering from myocardial infarction. In some embodiments, the pharmaceutical composition comprises argatroban. In some embodiments, a dosage of 0.1 to 5 mg/kg of argatroban is administered to the patient. In some embodiments, the patient reaches an anticoagulated state in less than 30 minutes after initiating the administration of the pharmaceutical composition. In some embodiments, the patient returns from an anticoagulated state to a normal coagulation state in 1 hour to 8 hours after initiating the administration of the pharmaceutical composition.

In another aspect, the patient is suffering from atrial fibrillation. In some embodiments, the pharmaceutical composition comprises LMWH. In some embodiments, a dosage of 0.05 to 150 mg/kg of LMWH is administered to the patient. In some embodiments, the patient reaches an anticoagulated state in less than 30 minutes after initiating the administration of the pharmaceutical composition. In some embodiments, the patient returns from an anticoagulated state to a normal coagulation state in 1 hour to 8 hours after initiating the administration of the pharmaceutical composition.

In another aspect, the patient is undergoing heart valve replacement. In some embodiments, the pharmaceutical composition comprises argatroban. In some embodiments, a dosage of 0.1 to 150 mg/kg of argatroban is administered to the patient. In some embodiments, the patient reaches an anticoagulated state in less than 30 minutes after initiating the administration of the pharmaceutical composition. In some embodiments, the patient returns from an anticoagulated state to a normal coagulation state in 1 hour to 8 hours after initiating the administration of the pharmaceutical composition.

In another aspect, the patient is suffering from coronary heart disease. In some embodiments, the patient is ineligible for coronary artery bypass graft (CABG) surgery. In some embodiments, the pharmaceutical composition comprises argatroban. In some embodiments, a dosage of 0.1 to 150 mg/kg of argatroban is administered to the patient. In some embodiments, the patient reaches an anticoagulated state in less than 30 minutes after initiating the administration of the pharmaceutical composition. In some embodiments, the patient returns from an anticoagulated state to a normal coagulation state in 1 hour to 8 hours after initiating the administration of the pharmaceutical composition.

In another aspect, the patient is undergoing a heart transplant. In some embodiments, the pharmaceutical composition comprises argatroban. In some embodiments, a dosage of 0.1 to 150 mg/kg of argatroban is administered to the patient. In some embodiments, the patient reaches an anticoagulated state in less than 30 minutes after initiating the administration of the pharmaceutical composition. In some embodiments, the patient returns from an anticoagulated state to a normal coagulation state in 1 hour to 8 hours after initiating the administration of the pharmaceutical composition.

In some embodiments, the method reduces blood clotting in treatment of acute coronary syndrome.

In another aspect, described herein is a unit dose comprising a unit dose receptacle, wherein the unit dose receptacle comprises a pharmaceutical composition comprising at least one anticoagulant or antiplatelet agent disclosed herein.

In yet another aspect, described herein is a kit, comprising: a container comprising the pharmaceutical composition disclosed herein; and an aerosolization device or an inhaler. In some embodiments, the kit comprises a container comprising the unit dose disclosed herein; and an aerosolization device or an inhaler.

A non-invasive method to administer and maintain effective therapeutic concentrations of an antiplatelet agent or anticoagulant has been developed, thereby enabling self-administration of the drug both in an ambulatory and hospital setting. Inhalation can be one of the shortest routes for a drug to reach the heart. The inhalation route has the ability to direct a bolus drug many times higher in concentration to the target—coronary arteries and yet keeps the overall body exposure lower than current therapies. Drugs administered via the IV route are significantly diluted in the venous blood volume and lungs before reaching the cardiac circulation. Drugs delivered by inhalation exhibit rapid peak drug concentrations in the coronary arteries where the drug is required and maintained at therapeutic levels. The method has advantages as compared to conventional drug delivery technologies for acute administration can be made available for chronic use.

The non-invasive method is useful to prevent platelet aggregation as a prophylaxis for ischemic heart conditions, quickly achieving and maintaining therapeutic levels of drug in the coronary arteries, with a pulsatile pharmacokinetic profile and transient pharmacodynamic effect mimicking the effect of an IV. The method delivers high drug concentrations that are safe and effective to the heart and the overall exposure to the body. Although the delivery of medications through the lung for systemic effect is not new, it was thought the method would not be effective for delivery to the heart, because of the fast passage of drug. Surprising effective dug concentrations in the coronary arteries are achieved.

The method is also useful to prevent clot formation as a prophylaxis for ischemic heart conditions and atrial fibrillation. The method quickly achieves and maintains therapeutic levels of drug in the left atrium (where clots are formed in AF patients) and coronary arteries (where clots are formed in patients with ACS), with high drug concentrations that are safe and effective to the heart and the overall exposure to the body.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Definitions

Figure 1:
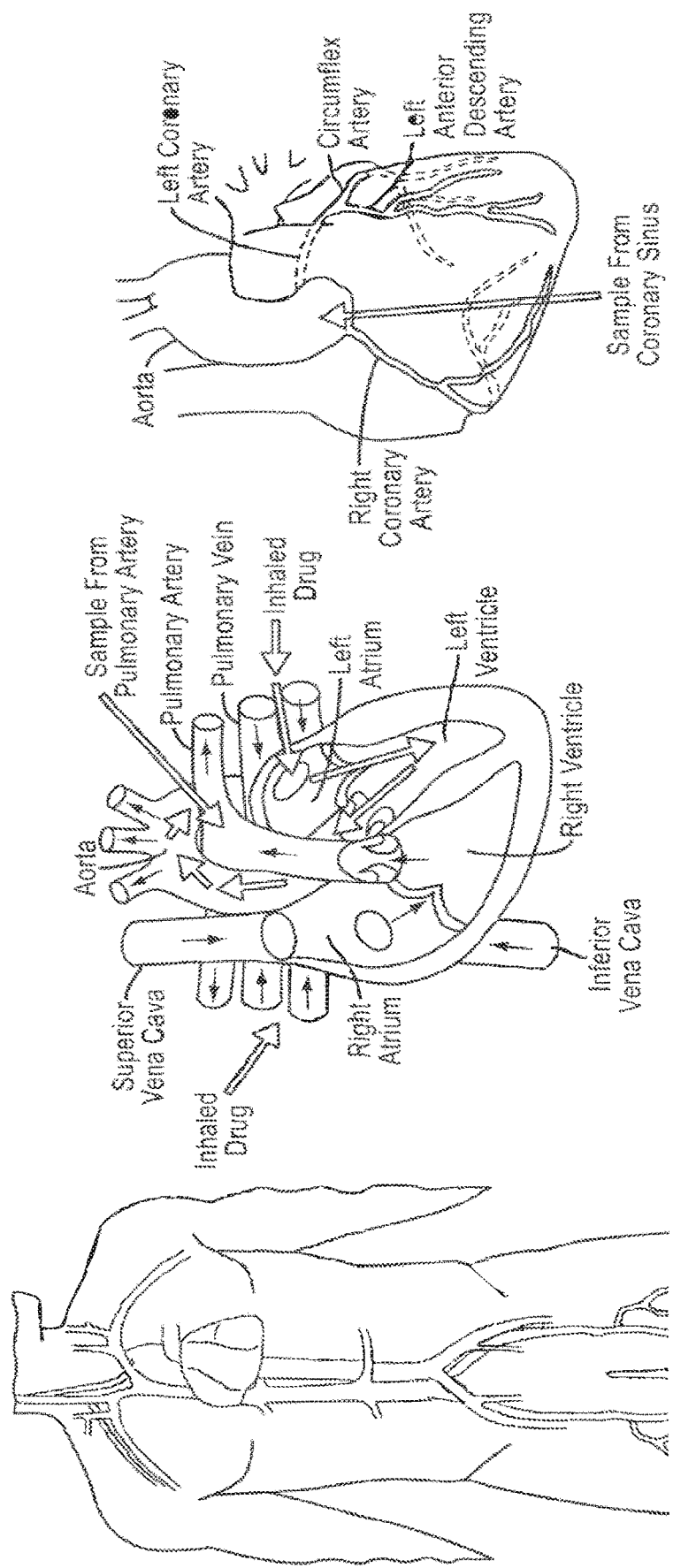
FIG. 1 shows how inhaled drug of the present invention passes through directly from the lungs to coronary arteries.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "an indication" includes a plurality of such indications and reference to "the drug" includes reference to one or more drugs known to those skilled in the art, and so forth.

The terms "subject," "patient," and "individual" are used herein interchangeably to include a human or animal. For example, the animal subject may be a mammal, a primate (e.g., a monkey), a livestock animal (e.g., a horse, a cow, a sheep, a pig, or a goat), a companion animal (e.g., a dog, a cat), a laboratory test animal (e.g., a mouse, a rat, a guinea pig, a bird), an animal of veterinary significance, or an animal of economic significance.

The term "administering" as used herein includes oral administration, topical contact, administration as a suppository, intravenous, intratracheal, intraperitoneal, intramuscular, intralesional, intrathecal, intranasal, or subcutaneous administration to a subject. Administration is by any route, including via pulmonary administration (e.g. inhalation).

The term "solvate" are used herein interchangeably to include pharmaceutically acceptable solvates. For example, a pharmaceutically acceptable solvate is intended to include, but is not limited to, a solvate that retains one or more of the biological activities and/or properties of the at least one anticoagulant or antiplatelet agent and that is not biologically or otherwise undesirable. Examples of pharmaceutically acceptable solvates include, but are not limited to, anticoagulant or antiplatelet agent in combination with water, isopropanol, ethanol, methanol, DMSO, ethyl acetate, acetic acid, ethanolamine, or combinations thereof.

The term "salt" are used herein to include pharmaceutically acceptable salts. For example, a pharmaceutically acceptable salt is intended to include, but are not limited to, salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methanesulfonates, propanesulfonates, naphthalene-1-sulfonates, naphthalene-2-sulfonates, and mandelates.

The term "about" in relation to a reference numerical value can include a range of values plus or minus 10% from that value. For example, the amount "about 10" includes amounts from 9 to 11, including the reference numbers of 9, 10, and 11. The term "about" in relation to a reference numerical value can also include a range of values plus or minus 10%, 9%, 8%, 7%, 6%, 5%, 4%, 3%, 2%, or 1% from that value.

As used herein, "mass median aerodynamic diameter" or "MMAD" refers to the median aerodynamic size of a plurality of particles or particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. As used herein, MMAD refers to the median of the aerodynamic particle or particle size distribution of aerosolized particles determined by cascade impaction, unless the context indicates otherwise.

As used herein, "effective amount" refers to an amount covering both therapeutically effective amounts and prophylactically effective amounts. Also as used herein, a "therapeutically effective amount" of an active agent refers to an amount that is effective to achieve a desired therapeutic result. A therapeutically effective amount of a given active agent will typically vary with respect to factors such as the type and severity of the disorder or disease being treated and the age, gender, and weight of the patient. Unless otherwise specified, the term "therapeutically effective amount" includes a "prophylactically effective amount," i.e., an amount of active agent that is effective to prevent the onset or recurrence of a particular condition, disease, or disorder in a susceptible individual.

II. Disease or Disorders to be Treated

The clinical presentations of ischemic heart disease can include silent ischemia, stable angina pectoris, unstable angina (UA), myocardial infarction (MI), heart failure, and sudden death. The acute coronary syndromes can encompass a spectrum of unstable coronary artery disease and denote episodes of acute myocardial ischemia due to impaired coronary blood flow. Differentiating itself from conditions such as stable angina and heart failure, ACS can be a manifestation of CAD and encompass unstable angina, non-ST elevated myocardial infarction (NSTEMI) and ST elevated myocardial infarction (STEMI). The unification of these types of coronary artery disease under a single term can reflect the understanding that they are all caused by a similar pathophysiology or sequence of pathologic events characterized by erosion, fissuring, or rupture of a preexisting plaque, leading to thrombosis (clotting) within the coronary arteries and impaired blood supply to the heart muscle. The classic clinical presentation of ACS can be also similar and typically consists of retrosternal pain or heaviness radiating to the neck, jaw, or left arm and often accompanied by other symptoms such as diaphoresis, nausea, and dyspnea. In most cases acute coronary syndromes can be first classified, according to presentation on an electrocardiogram (ECG) into ST elevated ACS and non-ST elevated ACS. Later, according to the presence of cardiac biomarkers, ACS can be classified into unstable angina (UA) and myocardial infarction (MI). Myocardial infarction can be then further distinguished to non-ST segment elevated myocardial infarction (NSTEMI) and ST segment elevated myocardial infarction (STEMI) giving the final three diagnoses: UA, NSTEMI and STEMI.

The initiation of an acute coronary syndrome (ACS) can be the disruption of an atheromatous plaque, but the actual process that eventually leads to ACS can begin to develop early in life and progresses with time—this process can be called atherosclerosis. Atherosclerosis can involve chronic inflammatory response in the walls of arteries, in large part due to the deposition of lipoproteins and it can be commonly referred to as a "hardening" or "furring" of the arteries. This process can eventually result in formation of multiple plaques within the arteries.

Plaque can be a complex structure made up of a combination of cholesterol, other fatty materials, calcium, and blood components that stick to the artery wall lining. Plaques can be present in different shapes and sizes and they can form a type of hard shell or scar-like covering.

Pathologically, plaque can be divided into three distinct components: 1) The atheroma is the nodular accumulation of a soft, flaky, yellowish material at the center of large plaques, composed of macrophages nearest the lumen of the artery; 2) Underlying areas of cholesterol crystals; and 3) Calcification at the outer base of older/more advanced lesions. Chronic progression of atherosclerosis can result in either plaque ruptures and, as a result, stenosis of the artery, or if the compensating artery enlargement process is excessive, then a net aneurysm results. During their lifetime, the most coronary plaques can remain quiescent, while only very few will become complicated by clinically significant thrombosis. These plaques are rare, but because they are thrombosis-prone they can be highly dangerous and can be labeled vulnerable or unstable plaque. Therefore, vulnerable plaque is a plaque that can be assumed to be at high short-term risk of thrombosis, which can cause an ACS.

Atherosclerotic plaque can require 10-15 years to develop fully. There are several stages of atherosclerosis: Stary I lesion: the endothelium also expresses surface adhesion molecules E selectin and P selectin, attracting more polymorphonuclear cells and monocytes in the subendothelial space; Stary II lesion: macrophages begin to take up large amounts of low-density lipoprotein (LDL) (fatty streak); Stary III lesion: as the process continues, macrophages eventually become foam cells; Stary IV lesion: lipid exudes into the extracellular space and begins to coalesce to form the lipid core; Stary V lesion: smooth muscle cells (SMCs) and fibroblasts move in, forming fibroatheromas with soft inner lipid cores and outer fibrous caps; Stary VI lesion: rupture of the fibrous cap with resultant thrombosis causes ACS; and Stary VII and VIII lesions: as lesions stabilize, they become fibrocalcific (Stary VII lesion) and, ultimately, fibrotic with extensive collagen content (Stary VIII lesion).

Thrombosis can be the formation of a clot or thrombus inside a blood vessel, obstructing the flow of blood through the circulatory system. Coronary thrombosis in ACS can develop at the site of a vulnerable plaque. The lipid-rich core exposed after plaque rupture can be highly thrombogenic and can have a high concentration of tissue factor. Thrombosis can be induced at the site of plaque rupture or erosion and can lead to rapid changes in the severity of stenosis that can cause subtotal or total vessel occlusion. The thrombus can be fibrin-rich and completely occlusive in STEMI, and platelet-rich and partially or intermittently occlusive in NSTEMI. It is important to note that thrombi can be formed by plaque rupture as well as plaque erosion. It can occur in a heterogeneous group of plaques where no deep injury exists to explain the overlying thrombus, and only the endothelium is missing at the plaque-thrombus interface.

In cases of platelet-rich thrombi in particular, it can be also possible to spontaneously dissolve these through thrombolysis. This can cause transient episodes of thrombotic vessel occlusion and associated transient ischemia. Thrombolysis in this case can cause thrombus fragmentation, embolization and occlusion of downstream arterioles and capillaries which in return can create small areas of necrosis and subsequent SLAM (signaling lymphocytic activation molecule) or/and transient release of cardiac markers.

Inhalation can also be used to deliver drug for prophylaxis of ischemic heart conditions (e.g.: post PTCA, CABG, UA, etc). Exemplary advantages over IV administration are shown in Table 1.

TABLE 1

Comparison of IV versus Pulmonary Administration

| IV Administration | Pulmonary administration |
| --- | --- |
| Administration requires a hospital setting | Administration can be in an ambulatory of hospital setting |
| A physician or paramedic is required for administration | Self-administration of medication |
| Only acute administration is feasible | Both acute and chronic administrations are feasible |
| Invasive procedure requiring a needle | Non-invasive procedure of administration |
| Drug is diluted before it reaches the coronary arteries | Drug is targeted to the coronary arteries prior to dilution |
| Peak arterial concentrations are lower than venous concentrations with overall exposure at high drug concentrations | Peak arterial concentrations are higher than venous concentrations with the potential for overall exposure to body being lower than IV |

The lung can be one of the shortest routes for drug to the coronary arteries with minimal dilution other than injecting the drug directly into the coronaries during a PTCA or PCI procedure or CABG surgery. Drugs delivered via the lung can have the quickest onset action compared to those delivered via the oral route. Pulmonary drug delivery to the heart can be better than intravenous injection as the drug targets the coronary arteries where it is primarily required as preventative to any ischemic conditions.

Thrombolytic therapy can be used in myocardial infarction, cerebral infarction, and, on occasion, in massive pulmonary embolism. The main risk can be bleeding. In some cases, treatment should not be given to patients having had recent bleeding, uncontrolled hypertension or a hemorrhagic stroke, or surgery or other invasive procedures within the previous 10 days.

III. Therapeutic Agents to be Delivered by Inhalation

Anticoagulants and antiplatelet agents can be used as therapeutic agents delivered via the pulmonary route and/or delivered by inhalation.

(a) Anticoagulants

Anticoagulants, a class of drugs that work to prevent the coagulation (clotting) of blood, can be used in methods, kits, and pharmaceutical compositions disclosed herein. Anticoagulants can occur naturally in leeches and/or blood-sucking insects. Anticoagulants can be inhaled by a subject as a medication for thrombotic disorders.

Anticoagulants can include, but are not limited to, coumarins (e.g., vitamin K antagonists), heparin (including low-molecular-weight heparin—LMWH), synthetic pentasaccharide inhibitors of factor Xa, direct factor Xa inhibitors, direct thrombin inhibitors, and other types of anticoagulants.

Coumarins (e.g., Vitamin K Antagonists)

This class of anticoagulants, coumarins (e.g., warfarin), can be derived from coumarin, which can be found in many plants. Coumarins can be used in the prevention of thrombosis and thromboembolism. For example, warfarin is a synthetic derivative of dicoumarol, a 4-hydroxycoumarin-derived mycotoxin anticoagulant originally discovered in spoiled sweet clover-based animal feeds. Warfarin and related 4-hydroxycoumarin-containing molecules can decrease blood coagulation by inhibiting vitamin K epoxide reductase, an enzyme that recycles oxidized vitamin K1 to its reduced form after it has participated in the carboxylation of several blood coagulation proteins, mainly prothrombin and factor VII. Warfarin can be used to decrease the tendency for thrombosis or as secondary prophylaxis in those individuals who have already formed a blood clot (thrombus). Alternatively, warfarin can also be used to prevent formation of future blood clots and/or reduce the risk of embolism. Warfarin can be used in clinical indications including, but not limited to, atrial fibrillation, the presence of artificial heart valves, deep venous thrombosis, and pulmonary embolism, and myocardial infarctions. Other examples of coumarins including, but not limited to, acenocoumarol, phenprocoumon, atromentin, and phenindione, can also be used in methods, kits, and pharmaceutical compositions described herein.

Heparin and Low-Molecular-Weight Heparin (LMWH)

Heparins are polysaccharides that inhibit coagulation, the process whereby thrombosis occurs. They can activate antithrombin III, which blocks thrombin from clotting blood. Heparin can be used in vivo (e.g., by inhalation), and also in vitro to prevent blood or plasma clotting in or on medical devices. Natural heparin can consist of molecular chains of varying lengths, or molecular weights. In some embodiments, heparins have an average molecular weight of about 5 to 100 kilodaltons (kDa), for example, about 5-10 kDa, about 5-20 kDa, about 5-30 kDa, about 5-40 kDa, about 5-50 kDa, about 5-60 kDa, about 5-70 kDa, about 5-80 kDa, about 5-90 kDa, about 5-100 kDa, about 10-20 kDa, about 10-40 kDa, about 10-60 kDa, about 10-80 kDa, about 10-100 kDa, about 20-40 kDa, about 20-60 kDa, about 20-80 kDa, about 20-100 kDa, about 40-60 kDa, about 40-80 kDa, about 40-100 kDa, about 60-80 kDa, about 60-100 kDa, or about 80-100 kDa. For instance, polydisperse pharmaceutical-grade heparin can have an average molecular weight from about 5-40 kDa. In some embodiments, heparins have an average molecular weight of at least about 5 kDa, for example, at least about 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, or 100 kDa. In some embodiments, heparins have an average molecular weight of about 5 kDa, for example, about 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, or 100 kDa.

Low-molecular-weight heparins (LMWHs), in contrast, can consist of only short chains of polysaccharide. LMWHs can be obtained by various methods of fractionation or depolymerisation of polymeric heparin. In some embodiments, LMWHs have an average molecular weight of less than about 15 kDa, for example, less than about 0.1 k Da, 0.5 kDa, 1 kDa, 2 kDa, 3 kDa, 4 kDa, 5 kDa, 6 kDa, 7 kDa, 8 kDa, 9 kDa, 10 kDa, 11 kDa, 12 kDa, 13 kDa, 14 kDa, or 15 kDa. In some embodiments, LMWHs have an average molecular weight of about 0.1 to 15 kDa, for example, about 0.1-15 kDa, about 0.1-10 kDa, about 0.1-5 kDa, about 0.1-2 kDa, about 0.1-1 kDa, about 0.1-0.5 kDa, about 0.5-15 kDa, about 0.5-10 kDa, about 0.5-5 kDa, about 0.5-2 kDa, about 0.5-1 kDa, about 1-15 kDa, about 1-10 kDa, about 1-5 kDa, about 1-2 kDa, about 2-15 kDa, about 2-10 kDa, about 2-5 kDa, about 5-15 kDa, about 5-10 kDa, or about 10-15 kDa. In some embodiments, at least about 50%, for instance, at least about 50%, 55%, 60%, 65%, 70%, 75%, 80%, 85%, 90%, or 95% of all chains of LMWHs have a molecular weight less than 5 kDa. In some embodiments, at least about 50%, for instance, at least about 50%, 55%, 60%, 65%, 70%, 75%, 80%, 85%, 90%, or 95% of all chains of LMWHs have a molecular weight less than 8 kDa. In some embodiments, at least about 50%, for instance, at least about 50%, 55%, 60%, 65%, 70%, 75%, 80%, 85%, 90%, or 95% of all chains of LMWHs have a molecular weight less than 10 kDa.

LMWH can be used as an anticoagulant in diseases that feature thrombosis, as well as for prophylaxis in situations that lead to a high risk of thrombosis. Thrombosis or thrombotic disease can be the formation of a clot within a blood vessel which interferes with the blood supply to tissues and causes problems such as deep vein thrombosis, pulmonary embolism when it is located in the veins, or heart attacks and strokes when located in the arteries.

Heparin can be derived from natural sources, mainly porcine intestine or bovine lung, can be administered therapeutically to prevent thrombosis. However, the effects of natural or unfractionated heparin can be difficult to predict. After a standard dose of unfractionated heparin, coagulation parameters must be monitored very closely to prevent over- or under-anticoagulation.

The coagulation cascade is a normal physiological process which aims at preventing significant blood loss or hemorrhage following vascular injury. Unfortunately, there are times when a blood clot (thrombus) will form when it is not needed. For instance, some high risk conditions such as acute medical illness prolonged immobilization, surgery, or cancer can increase the risk of developing a blood clot which can potentially lead to significant consequences. The coagulation cascade can consist of a series of steps in which a protease cleaves and subsequently activates the next protease in the sequence. Since each protease can activate several molecules of the next protease in the series, this biological cascade can be amplified. The final result of these reactions can be to convert fibrinogen, a soluble protein, to insoluble threads of fibrin. Together with platelets, the fibrin threads can form a stable blood clot.

Antithrombin (AT), a serine protease inhibitor, is the major plasma inhibitor of coagulation proteases. LMWHs inhibit the coagulation process through binding to AT via a pentasaccharide sequence. This binding leads to a conformational change of AT which accelerates its inhibition of thrombin (e.g., factor I Ia) and activated factor X (e.g., factor Xa). Once dissociated, the LMWH can be free to bind to another antithrombin molecule and subsequently inhibit more thrombin. The effect of LMWH can be monitored by the anti-factor Xa assay, measuring anti-factor Xa activity. In an anti-factor Xa assay, patient plasma can be added to a known amount of excess factor Xa and excess antithrombin. If heparin or LMWH is present in the patient plasma, it can bind to antithrombin and form a complex with factor Xa, inhibiting it. The amount of residual factor Xa can be inversely proportional to the amount of heparin and/or LMWH in the plasma. The amount of residual factor Xa can be detected by adding a chromogenic substrate that mimics the natural substrate of factor Xa, making residual factor Xa cleave it, releasing a colored compound that can be detected by a spectrophotometer. Antithrombin deficiencies in the patient do not affect the assay, because excess amounts of antithrombin is provided in the reaction. Results are given in anticoagulant concentration in units/mL of anti-factor Xa, such that high values indicate high levels of anticoagulation and low values indicate low levels of anticoagulation. In some embodiments, LMWHs have a potency of greater than about 10 units/mg of anti-factor Xa activity, for example, greater than about 10, 15, 20, 25, 30, 35, 40, 45, 50, 55, 60, 65, 70, 75, 80, 85, 90, 95 or 100 units/mg of anti-factor Xa activity. In some embodiments, LMWHs have a ratio of anti-factor Xa activity to anti-thrombin activity of more than about 1.0, for example more than about 1.0, 1.1, 1.2, 1.3, 1.4, 1.5, 1.6, 1.7, 1.8, 1.9, or 2.0.

Various methods of heparin depolymerisation can be used in the manufacture of low-molecular-weight heparin, including: 1) Oxidative depolymerisation with hydrogen peroxide, e.g., used in the manufacture of ardeparin (Normiflo); 2) Deaminative cleavage with isoamyl nitrite, e.g., used in the manufacture of certoparin (Sandoparin); 3) Alkaline beta-eliminative cleavage of the benzyl ester of heparin, e.g. used in the manufacture of enoxaparin (Lovenox and Clexane); 4) Oxidative depolymerisation with Cu2+ and hydrogen peroxide, e.g., used in the manufacture of pamaparin (Fluxum); 5) Beta-eliminative cleavage by the heparinase enzyme, e.g., used in the manufacture of tinzaparin (Innohep and Logiparin); and 6) Deaminative cleavage with nitrous acid, e.g., used in the manufacture of dalteparin (Fragmin), reviparin (Clivarin) and nadroparin (Fraxiparin).

LMWHs prepared by similar processes can vary in their properties. In one example, Dalteparin and Nadroparin are more similar than products produced by different processes. In another example, however, enoxaparin and tinzaparin are different from each other with respect to chemical, physical, and biological properties. In some cases, a slight change in the depolymerisation process could result into substantial variation of the structure or composition of a given LMWH.

Differences between heparin (e.g. "unfractioned heparin") and LMWH can include: Average molecular weight: heparin can be about 15 kDa and LMWH can be about 4.5 kDa; less frequent subcutaneous dosing than for heparin for postoperative prophylaxis of venous thromboembolism; once or twice daily subcutaneous injection for treatment of venous thromboembolism and in unstable angina instead of intravenous infusion of high dose heparin; no need for monitoring of the APTT coagulation parameter as required for high dose heparin; possibly a smaller risk of bleeding; smaller risk of osteoporosis in long-term use; smaller risk of heparin-induced thrombocytopenia, a potential side effect of heparin; the anticoagulant effects of heparin are typically reversible with protamine sulfate, while protamine's effect on LMWH is limited; has less of an effect on thrombin compared to heparin, but about the same effect on Factor Xa.

Because it can be given subcutaneously and does not require APTT monitoring, LMWH can permit outpatient treatment of conditions such as deep vein thrombosis or pulmonary embolism that previously mandated inpatient hospitalization for unfractionated heparin administration. Also because LMWH has more predictable pharmacokinetics and anticoagulant effect, LMWH can be preferred over unfractionated heparin for patients with massive pulmonary embolism and for initial treatment of deep vein thrombosis. In some embodiments, prophylactic treatment of hospitalized medical patients with LMWH and/or similar anticoagulants can result in a 53% reduction of risk for symptomatic deep vein thrombosis.

Many of these agents have been evaluated as anticoagulants in acute coronary syndrome (ACS) managed by percutaneous intervention (PCI). In some cases, the use of LMWH needs to be monitored closely in patients at extremes of weight or in-patients with renal dysfunction. An anti-factor Xa activity can be useful for monitoring anticoagulation. In some embodiments, in patients with malignancy and acute venous thromboembolism, dalteparin can be more effective than coumadin in reducing the risk of recurrent embolic events. Use of LMWH in cancer patients for at least the first 3 to 6 months of long-term treatment is recommended in numerous guidelines and is now regarded as a standard of care.

Synthetic Pentasaccharide Inhibitors of Factor Xa

Synthetic pentasaccharide inhibitors of factor Xa can be used in methods, kits, and pharmaceutical compositions disclosed herein. For example, fondaparinux, a smaller molecule than low molecular weight heparin, is a synthetic sugar composed of the five sugars (pentasaccharide) in heparin that bind to antithrombin.

Idraparinux, which has a similar chemical structure and the same method of action as fondaparinux, has an elimination half-life about five to six times longer. For example, elimination half-life of idraparinux is increased from fondaparinux's 17 hours to approximately 80 hours. In some cases, idraparinux can be administered only once a week.

Direct Factor Xa Inhibitors

Direct factor Xa inhibitors, a class of anticoagulant drugs that act directly upon Factor X in the coagulation cascade without using antithrombin as a mediator, can be used in methods, kits, and pharmaceutical compositions disclosed herein. Examples of direct factor Xa inhibitors, include but are not limited to, Rivaroxaban (Xarelto), Apixaban (Eliquis), Edoxaban (Savaysa), Betrixaban (LY517717), Darexaban (YM150), TAK-442, eribaxaban (PD0348292), and Otamixaban.

In some cases, direct factor Xa inhibitors demonstrated efficacy and safety against warfarin for stroke prevention in atrial fibrillation. In some cases, direct factor Xa inhibitors demonstrated efficacy and safety against low-molecular-weight heparin for treatment and/or secondary prevention of venous thromboembolism and/or for initial treatment and prevention of venous thromboembolism in patients undergoing hip or knee replacement.

Direct Xa inhibitors can have a rapid onset and offset of action which reduces need for bridging with a parenteral anticoagulant. In some cases, direct Xa inhibitors do not require frequent monitoring.

In some cases, direct Xa inhibitors do not require re-dosing whilst having few strong drug interactions and no food interactions. In some cases, direct Xa inhibitors demonstrated a lower risk of intra cranial bleeding in trials. These advantages can lead to greater convenience by patients and doctors.

Direct Thrombin Inhibitors

Direct thrombin inhibitors (DTI), a class of medication that act as anticoagulants (e.g., delaying blood clotting) by directly inhibiting the enzyme thrombin (factor II), can be used in methods, kits, and pharmaceutical compositions disclosed herein.

There can be three types of DTis, dependent on their interaction with the thrombin molecule. Bivalent DTis (e.g., hirudin and analogs) can bind both to the active site and exosite 1, univalent DTis can bind only to the active site, and the allosteric inhibitors are the third class of inhibitors.

Examples of bivalent DTis, include but are not limited to, Hirudin, Bivalirudin, Lepirudin, and Desirudin. Examples of univalent DTis, include but are not limited to, Argatroban, Melagatran (and its prodrug ximelagatran), and Dabigatran. Examples of the allosteric inhibitors, include but are not limited to, DNA aptamers, benzofuran dimers, benzofuran trimers, as well as polymeric lignins. For example, a new sulfated-O4 lignin (SbO4L) has been discovered which has shown a dual mechanism of action for anti-thrombosis. This SbO4L can show allosteric inhibition of thrombin for fibrinogen, while providing a competitive inhibition of thrombin interaction with platelet glycoprotein Iba (GPiba), thereby preventing thrombin mediated platelet aggregation.

Other Types of Anticoagulants

Other types of anticoagulants can be used in methods, kits, and pharmaceutical compositions disclosed herein. In one example, Batroxobin, a toxin from a snake venom, can clots platelet-rich plasma without affecting platelet functions (e.g., lyses fibrinogen) and can be used in methods, kits, and pharmaceutical compositions disclosed herein. In another example, Hementin, an anticoagulant protease from the salivary glands of the giant Amazon leech (Haementeria ghilianii), can also be used in methods, kits, and pharmaceutical compositions disclosed herein.

(b) Antiplatelet Agents

Antiplatelet agents, a class of pharmaceuticals that decrease platelet aggregation and/or inhibit thrombus formation, can be used in methods, kits, and pharmaceutical compositions disclosed herein. Antiplatelet agents can be effective in the arterial circulation. In some cases, antiplatelet agents can be used in primary and/or secondary prevention of thrombotic cerebrovascular and/or cardiovascular disease.

Treatment of established arterial thrombosis can include the use of Antiplatelet agents and thrombolytic therapy. Antiplatelet agents can alter the platelet activation at the site of vascular damage crucial to the development of arterial thrombosis.

Antiplatelet agents can include, but are not limited to, Irreversible cyclooxygenase inhibitors (e.g., COX inhibitors), Adenosine diphosphate (ADP) receptor inhibitors, Phosphodiesterase inhibitors, Protease-activated receptor-I (PAR-I) antagonists, Glycoprotein lib/IIIa inhibitors, Adenosine reuptake inhibitors, and Thromboxane inhibitors.
Irreversible Cyclooxygenase Inhibitors (e.g., COX Inhibitors)

Irreversible cyclooxygenase inhibitors (e.g., COX inhibitors) can be used in methods, kits, and pharmaceutical compositions disclosed herein. COX inhibitors are a form of non-steroidal anti-inflammatory drug (NSAID) that can directly target cyclooxygenase-2, COX-2, an enzyme responsible for inflammation and pain. Targeting selectivity for COX-2 can reduce the risk of peptic ulceration, and can be the main feature of celecoxib, rofecoxib and other members of this drug class.

Aspirin and Triflusal can irreversibly inhibit the enzyme COX, resulting in reduced platelet production of Thromboxane A2 (TXA2). TXA2, a type of thromboxane, is a powerful vasoconstrictor that can lower cyclic AMP and/or can initiate the platelet release reaction.
Adenosine Diphosphate (ADP) Receptor Inhibitors Adenosine diphosphate (ADP) receptor inhibitors, a class of antiplatelet agents, can be used in methods, kits, and pharmaceutical compositions disclosed herein. These drugs inhibit some or all types of adenosine diphosphate receptors (e.g., P2Y receptors). P2Y receptors are a family of purinergic G protein-coupled receptors, can be stimulated by nucleotides such as ATP, ADP, UTP, UDP and UDP-glucose. For example, inhibitors of the receptor subtype P2Y12 are one class of P2Y receptor inhibitors. Adenosine diphosphate (ADP) receptor inhibitors include, but are not limited to, Clopidogrel (Plavix), Prasugrel (Effient), Ticlopidine (Ticlid), Ticagrelor (Brilinta), Cangrelor, and Elinogrel. In one instance, Clopidogrel affects the ADP-dependent activation of lib/IIIa complex. In another instance, ticagrelor, a cyclopentyltriazolopyrimidine (CPTP), is a P2Y12 receptor inhibitor.
Phosphodiesterase Inhibitors Phosphodiesterase inhibitors can be used in methods, kits, and pharmaceutical compositions disclosed herein. For example, Vorapaxar (Zontivity) is a thrombin receptor (protease-activated receptor, PAR-I) antagonist based on the natural product himbacine. [0101]

In one example, the phosphodiesterase inhibitor is Cilostazol (Pletal), which is a quinolinone-derivative medication that can be used in the alleviation of the symptom of intermittent claudication in individuals with peripheral vascular disease. Cilostazol can have therapeutic focus on cyclic adenosine monophosphate (cAMP). It can inhibit platelet aggregation and can be a direct arterial vasodilator. The main effects of Cilostazol can be dilation of the arteries (e.g. supplying blood to the legs) and decreasing platelet coagulation.
Glycoprotein IIb/IIIa Inhibitors Glycoprotein IIb/IIIa inhibitors, a class of antiplatelet agents, can be used in methods, kits, and pharmaceutical compositions disclosed herein. Glycoprotein IIb/IIIa inhibitors include, but are not limited to, Abciximab (ReoPro), Eptifibatide (Integrilin), Tirofiban (Aggrastat), roxifiban, and orbofiban. Glycoprotein IIb/IIIa inhibitors can block a receptor on the platelet for fibrinogen and/or von Willebrand factor 3 classes. In some embodiments, the Glycoprotein IIb/IIIa inhibitor is a murine-human chimeric antibody (e.g., abciximab). In some embodiments, the Glycoprotein IIb/IIIa inhibitor is a synthetic peptide (e.g., eptifibatide). In some embodiments, the Glycoprotein IIb/IIIa inhibitor is a synthetic non-peptide (e.g., tirofiban). In some embodiments, the Glycoprotein IIb/IIIa inhibitor is epoprostenol, which is a prostacyclin that can be used to inhibit platelet aggregation during renal dialysis (with or without heparin) and can be also used in primary pulmonary hypertension. In some embodiments, the Glycoprotein IIb/IIIa inhibitor is streptokinase, which forms a complex with plasminogen, resulting in a conformational change that activates other plasminogen molecules to form plasmin. In some embodiments, the Glycoprotein IIb/IIIa inhibitor is plasminogen activators (PA) and/or tissue-type plasminogen activators (e.g., alteplase, tenecteplase), which can be produced by recombinant technology.

Glycoprotein IIb/IIIa inhibitors can be used during percutaneous coronary intervention (e.g., angioplasty with or without intracoronary stent placement). Glycoprotein IIb/IIIa inhibitors can prevent platelet aggregation and/or thrombus formation by inhibition of the GpIIb/IIIa receptor on the surface of the platelets. Glycoprotein IIb/IIIa inhibitors can also be used to treat acute coronary syndromes, without percutaneous coronary intervention, depending on TIMI risk.

In one example, the Glycoprotein IIb/IIIa inhibitor is Tirofiban, which is a synthetic, non-peptide inhibitor acting at glycoprotein (GP) IIb/IIIa receptors in human platelets to inhibit platelet aggregation. Tirofiban can be sold in parenteral dosage forms containing 5 mg or 12.5 mg, respectively. Tirofiban can have a rapid onset and short duration of action after proper IV administration. Coagulation parameters can turn to normal 4 to 8 hours after the drug is withdrawn. Tirofiban in combination with heparin and aspirin can be indicated in the management of patients with unstable angina or non-Q-wave myocardial infarction, including patients who may subsequently undergo percutaneous transluminal coronary angioplasty (PICA), to decrease the rate of refractory ischemic conditions, new myocardial infarction and death. A mathematical evaluation of the pk of Tirofiban shows it can have a different and favorable pk profile compared to the IV and can offer prolonged prophylaxis for ischemic heart conditions.
Adenosine Reuptake Inhibitors Adenosine reuptake inhibitors can be used in methods, kits, and pharmaceutical compositions disclosed herein. An adenosine reuptake inhibitors (AdoRI) is a type of drug which can act as a reuptake inhibitor for the purine nucleoside and neurotransmitter adenosine by blocking the action of one or more of the equilibrative nucleoside transporters (ENTs). This can in turn lead to increased extracellular concentrations of adenosine and therefore an increase in adenosinergic neurotransmission. Adenosine reuptake inhibitors can include, but are not limited to, Acadesine, Acetate, Barbiturates, Benzodiazepines, Calcium channel blockers, Carbamazepine, Carisoprodol, Cilostazol, Cyclobenzaprine, Dilazep, Dipyridamole (Persantine), Estradiol, Ethanol, Flumazenil, Hexobendine, Hydroxyzine, Indomethacin, Inosine, KF24345, Meprobamate, Nitrobenzylthioguanosine, Nitrobenzylthioinosine, Papaverine, Pentoxifylline, Phenothiazines, Phenytoin, Progesterone, Propentofylline, Propofol, Puromycin, R75231, RE 102 BS, Soluflazine, Toyocamycin, Tracazolate, and Tricyclic antidepressants. In one example, the adenosine reuptake inhibitor is Dipyridamole (Persantine), which inhibits platelet phosphodiesterase, causing an increase in cyclic AMP with potentiation of the action of PGI2-opposes actions of TX A2.

Thromboxane Inhibitors

Thromboxane inhibitors, a member of the family of lipids known as eicosanoids, can also be used in methods, kits, and pharmaceutical compositions disclosed herein.

The two major thromboxanes are thromboxane A2 and thromboxane B2. Thromboxane can act by binding to any of the thromboxane receptors, G-protein-coupled receptors coupled to the G protein $G_q$. Thromboxane can be a vasoconstrictor and/or a potent hypertensive agent, and can facilitate platelet aggregation. Thromboxane A2 (TXA2), produced by activated platelets, can have prothrombotic properties, stimulating activation of new platelets as well as increasing platelet aggregation. Platelet aggregation can be achieved by mediating expression of the glycoprotein complex GP IIb/IIIa in the cell membrane of platelets. Circulating fibrinogen can bind these receptors on adjacent platelets, further strengthening the clot.

Thromboxane inhibitors can inhibit the synthesis of thromboxane (e.g., Thromboxane synthesis inhibitors) and/or inhibit the target effect of thromboxane (e.g., thromboxane receptor antagonist). In one example, picotamide is both a thromboxane synthase inhibitor and a thromboxane receptor antagonist. In another example, terutroban is a thromboxane receptor antagonist.

IV. Pharmaceutical Compositions for Pulmonary Administration

The amount of at least one anticoagulant or antiplatelet agent in the pharmaceutical composition can vary. The amount of at least one anticoagulant or antiplatelet agent can be about 0.1% to 100% by weight of the total amount of the pharmaceutical composition. In some cases, the amount of at least one anticoagulant or antiplatelet agent is at least about 0.1% by weight of the total amount of the pharmaceutical composition, for example, at least about 0.1%, 0.2%, 0.3%, 0.4%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% by weight of the total amount of the pharmaceutical composition. In some cases, the amount of at least one anticoagulant or antiplatelet agent is about 0.1%-100% by weight of the total amount of the pharmaceutical composition, for example, about 0.1%-1%, 0.1%-5%, 0.1-10%, 0.1%-20%, 0.5%-1%, 0.5%-5%, 0.5%-10%, 0.5%-20%, 1%-5%, 1%-10%, 1%-20%, 5%-10%, 5%-20%, 10%-20%, 10%-30%, 20%-30%, 20%-40%, 30%-40%, 30%-50%, 40%-50%, 40%-60%, 50%-60%, 50%-70%, 60%-70%, 60%-80%, 70%-80%, 70%-90%, 80%-90%, 80%-95%, 90%-95%, 90%-99%, 90%-100%, 95%-99%, or 99%-100% by weight of the total amount of the pharmaceutical composition.

The method of treatment via inhalation can result in a pulsatile pharmacokinetic profile and transient pharmacodynamic effect mimicking the effect of an IV. The method can delivers high drug concentrations that are safe and effective to the heart, while the distribution to the rest of the body can result in the drug being diluted to sub-therapeutic levels. This method can be one of the shortest routes of delivery to the heart. This advantage can provide the convenience of self-administration like the "pill-in-the-pocket" approach, but the effectiveness and fast onset of action of an IV.

The subject can be a mammal in need thereof, preferably such mammal is a human patient. Examples of patients include, but are not limited to, pediatric patients, adult patients, and geriatric patients. In some embodiments, the pharmaceutical composition only intended and used in a prophylactic treatment to prevent a disease (e.g., acute coronary syndrome) from occurring.

The at least one anticoagulant or antiplatelet agent can have a potency of greater than about 10 units/mg, for example, greater than about 10 units/mg, 15 units/mg, 20 units/mg, 25 units/mg, 30 units/mg, 35 units/mg, 40 units/mg, 45 units/mg, 50 units/mg, 60 units/mg, 70 units/mg, 80 units/mg, 90 units/mg, or 100 units/mg of anti-factor Xa activity. In some embodiments, the potency of anti-factor Xa activity can be measured by an anti-factor Xa assay. Anti-factor Xa assays can be used to measure levels of at least one anticoagulant or antiplatelet agent, such as heparin and/or low-molecular-weight heparin (LMWH). The anti-factor Xa assay can be a chromogenic assay. In some cases, the anti-factor Xa assay uses a factor Xa substrate onto which a chromophore has been linked and then the factor Xa cleaves the chromogenic substrate, releasing a colored compound that can be detected with a spectrophotometer, wherein the colored compound is directly proportional to the amount of factor Xa present. When a known amount of factor Xa is added to plasma containing heparin or LMWH, the heparin or LMWH enhances factor Xa inhibition by antithrombin rendering less factor Xa available to cleave the substrate. By correlating this result with a standard curve produced with known amounts of heparin or LMWH, the heparin or LMWH concentration in the plasma can be calculated.

The unit dose disclosed herein can comprise a unit dose receptacle and a pharmaceutical composition within the unit dose receptacle. The pharmaceutical composition comprises at least one anticoagulant or antiplatelet agent in an amount less than or equal to an amount of the same at least one anticoagulant or antiplatelet agent administered intravenously (e.g., in the arm) to achieve a minimum effective amount in the coronary sinus, and a pharmaceutically acceptable excipient. Examples of pharmaceutically acceptable excipients include, but are not limited to, lipids, metal ions, surfactants, amino, acids, carbohydrates, buffers, salts, polymers, and the like, and combinations thereof.

The unit dose of the pharmaceutical composition may be contained in a container, for example, a unit dose receptacle. Examples of containers include, but are not limited to, syringes, capsules, blow fill seal, blisters, vials, ampoules, bottles, or container closure systems made of metal, polymer (e.g., plastic, elastomer), glass, or the like. For instance, the vial may be a colorless Type I borosilicate glass ISO 6R 10 mL vial with a chlorobutyl rubber siliconized stopper, and rip-off type aluminum cap with colored plastic cover.

The unit dose can comprise at least about 0.1 mL of the pharmaceutical composition, for example, at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, or 100 mL of the pharmaceutical composition. The unit dose can comprise about 0.1-100 mL of the pharmaceutical composition, for example, about 0.1-0.2, 0.1-0.5, 0.1-1.0, 0.2-0.5, 0.2-1.0, 0.5-1.0, 0.5-1.5, 0.5-2.0, 0.5-3.0, 0.5-4.0, 0.5-5.0, 1.0-2.0, 1.0-3.0, 1.0-4.0, 1.0-5.0, 2.0-3.0, 2.0-4.0, 2.0-5.0, 3.0-5.0, 5-10, 10-20, 20-30, 30-40, 40-50, 50-60, 60-70, 70-80, 80-90, or 90-100 mL of the pharmaceutical composition. In some cases, the unit dose of the pharmaceutical composition ranges from about 2 ml to about 15 ml, such as from about 3 ml to about 10 ml, about 4 ml to about 8 ml, or about 5 ml to about 6 ml.

The pharmaceutical composition can be formulated as unit doses, distributed as the dosage unit or in a kit for use with a nebulizer, inhaler, metered dose inhaler, or dry powder inhaler. The unit dose can be in the form of a dry powder or a solution, either aqueous or non-aqueous, preferably pH buffered between 3 and 10, with a buffer such as citrate, phosphate, phthalate, or lactate, and optionally contains a preservative or de-aggregating agent such as a sugar or lipid. The unit dosage or kit may also include a propellant such as hydrofluoroalkane or chlorofluoralkane. The pharmaceutical composition can be in the form of a dry powder or a solution.

The container may be inserted into an aerosolization device (e.g., nebulizer). The container may be of a suitable shape, size, and material to contain the pharmaceutical composition and to provide the pharmaceutical composition in a usable condition.

As another example, at least one anticoagulant or antiplatelet agent may be prepared by lyophilizing at least one anticoagulant or antiplatelet agent to form a powder for storage. The powder is then reconstituted prior to use. This technique may be used when the at least one anticoagulant or antiplatelet agent is unstable in solution. The solvent for the solution to be lyophilized may comprise water. The solution may be excipient-free. For instance, the solution may be cryoprotectant-free. In one or more embodiments, a suitable amount (e.g., 30 mg per mL of final solution) of drug substance may be dissolved, e.g., in about the 75% of the theoretical total amount of water for injection under nitrogen bubbling. The dissolution time may be recorded and appearance may be evaluated. Then, the dilution to the final volume with water for injection (WFI) may be carried out. Final volume may be checked. Density, pH, endotoxin, bioburden, and content by UV may be measured both before and after sterile filtration.

The compositions of one or more embodiments of the present invention may be administered by inhalation. Moreover, the doses of composition that are inhaled can be much less than those administered by other routes and required to obtain similar effects. It may be due to the efficient targeting of the inhaled composition to the heart.

The dosage necessary and the frequency of dosing of the at least one anticoagulant or antiplatelet agent depend on the composition and concentration of the at least one anticoagulant or antiplatelet agent within the pharmaceutical composition. In some cases, the dose is less than its normal intravenous dose. In some cases, the dose is the same as its normal intravenous dose. In some cases, the dose is the same as the intracardiac dose.

Inhalation avoids the initial dilution of drug in the body as compared to intravenous or oral dosing. Inhalation also avoids first-pass metabolism, such as hepatic metabolism. Inhalation can allow rapid delivery of the at least one anticoagulant or antiplatelet agent to the heart as a bolus. Inhalation also avoids red blood cell metabolism. Inhalation can also avoid reduced blood pressure and fainting. With inhaled cardiotherapy the drug can be directed to the heart from the lungs as a bolus. So, the heart sees a high concentration. The drug can be rapidly diluted as it passes through the heart, but the exposure time is sufficient for the desired pharmacological action. Once the drug passes through the heart, the concentration of the drug in the overall blood can be below the therapeutic concentration and can be considered ineffective and thus safer. The therapeutic window can be the range of dosage of a drug or of its concentration in a bodily system that provides safe effective therapy. Anything below the minimum amount can be subtherapeutic and hence ineffective in that concentration. In view of the dilution, unwanted side effects can be minimized.

The dose can be administered during a single inhalation or may be administered during several inhalations. The fluctuations of the at least one anticoagulant or antiplatelet agent concentration can be reduced by administering the pharmaceutical composition more often or may be increased by administering the pharmaceutical composition less often. Therefore, the pharmaceutical composition of one or more embodiments of the present invention can be administered from about four times daily to about once a month, such as about once daily to about once every two weeks, about once every two days to about once a week, and about once a week to about once a month. In some embodiments, the pharmaceutical composition of the present invention can be administered about four times a day, about three times a day, about twice a day, about once a day, about three times a week, about twice a week, about once a week, about twice a month, or about once a month. The pharmaceutical composition can also be administered to the patient on an as-needed basis.

The dose of the at least one anticoagulant or antiplatelet agent delivered to a patient can range from about 0.1 mg to about 600 mg, such as from about 0.2 mg to 500 mg daily, depending on the condition being treated, the age and weight of the patient, and the like. In some cases, the at least one anticoagulant or antiplatelet agent can be administered daily. The daily dosage of the at least one anticoagulant or antiplatelet agent can range from about 0.1 mg to about 600 mg, such as about 0.5 mg to about 500 mg, about 1 mg to about 400 mg, about 2 mg to about 300 mg, and about 3 mg to about 200 mg.

For treating a patient suffering from acute coronary syndrome, the amount per dose of the at least one anticoagulant or antiplatelet agent administered can be an amount that is effective to treat the acute coronary syndrome. The amount of the at least one anticoagulant or antiplatelet agent can be at least about 0.001 mg/kg, such as at least about 0.001 mg/kg, 0.002 mg/kg, 0.003 mg/kg, 0.004 mg/kg, 0.005 mg/kg, 0.01 mg/kg, 0.02 mg/kg, 0.04 mg/kg, 0.06 mg/kg, 0.08 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, or 6 mg/kg. The amount of the at least one anticoagulant or antiplatelet agent can range from about 0.001 mg/kg to 6 mg/kg, such as from about 0.001 mg/kg to about 0.01 mg/kg, from about 0.01 mg/kg to about 0.05 mg/kg, from about 0.05 mg/kg to about 0.1 mg/kg, from about 0.1 mg/kg to about 0.2 mg/kg, from about 0.1 mg/kg to about 0.5 mg/kg, from about 0.1 mg/kg to about 1 mg/kg, from about 0.1 mg/kg to about 2 mg/kg, from about 0.1 mg/kg to about 3 mg/kg, from about 0.3 mg/kg to about 1 mg/kg, from about 0.3 mg/kg to about 2 mg/kg, from about 0.3 mg/kg to about 3 mg/kg, from about 0.5 mg/kg to about 1 mg/kg, from about 0.5 mg/kg to about 2 mg/kg, from about 0.5 mg/kg to about 3 mg/kg, from about 0.5 mg/kg to about 0.5 mg/kg to about 6 mg/kg, from about 0.7 mg/kg to about 1 mg/kg, from about 0.7 mg/kg to about 2 mg/kg, from about 0.7 mg/kg to about 4 mg/kg, from about 0.7 mg/kg to about 6 mg/kg, from about 1 mg/kg to about 2 mg/kg, from about 1 mg/kg to about 4 mg/kg, from about 1 mg/kg to about 6 mg/kg, from about 2 mg/kg to about 3 mg/kg, from about 2 mg/kg to about 4 mg/kg, from about 2 mg/kg to about 6 mg/kg, or from about 3 mg/kg to about 6 mg/kg.

The amount of the at least one anticoagulant or antiplatelet agent can be at least about 0.1 mg, such as at least about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, or 150 mg. The amount of the at least one anticoagulant or antiplatelet agent can range about 0.05-150 mg, such as about 0.05-150, 0.05-130, 0.05-110, 0.05-90, 0.05-70, 0.05-50, 0.05-30, 0.05-10, 0.05-5, 0.05-1, 0.05-0.5, 0.05-0.1, 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 mg. For example, the amount of the at least one anticoagulant or antiplatelet agent can range about from 0.1 to about 5 mg.

The concentration of the at least one anticoagulant or antiplatelet agent can be at least about 0.05 mg/mL, such as at least about 0.05, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, or 150 mg/mL. For example, the concentration of the at least one anticoagulant or antiplatelet agent can be at least about 30 mg/mL in a buffer. The concentration of the at least one anticoagulant or antiplatelet agent can range about 0.05-150 mg/mL, such as about 0.05-150, 0.05-130, 0.05-110, 0.05-90, 0.05-70, 0.05-50, 0.05-30, 0.05-10, 0.05-5, 0.05-1, 0.05-0.5, 0.05-0.1, 0.1-150, 0.1-130, 0.1-110, 0.1-90, 0.1-70, 0.1-50, 0.1-30, 0.1-10, 0.1-5, 0.1-1.0, 0.1-0.5, 1-150, 1-130, 1-110, 1-90, 1-70, 1-50, 1-30, 1-10, 1-5, 5-150, 5-130, 5-110, 5-90, 5-70, 5-50, 5-30, 5-10, 10-150, 10-130, 10-110, 10-90, 10-70, 10-50, 10-30, 30-150, 30-130, 30-110, 30-90, 30-70, 30-50, 50-150, 50-130, 50-110, 50-90, 50-70, 70-150, 70-130, 70-110, 70-90, 90-150, 90-130, 90-110, 110-150, 110-130, or 130-150 mg/mL. For example, the concentration of the at least one anticoagulant or antiplatelet agent can range about 30-50 mg/mL in a buffer.

In some instances, it is desirable to deliver a unit dose, such as doses of 0.1 mg or 100 mg or greater of the at least one anticoagulant or antiplatelet agent to the lung in a single inhalation. The above described phospholipid hollow and/or porous dry powder particles allow for doses of about 5 mg or greater, often greater than about 10 mg, sometimes greater than about 15 mg, sometimes greater than about 20 mg, sometimes greater than about 25 mg, and sometimes greater than about 30 mg, to be delivered in a single inhalation and in an advantageous manner. Alternatively, a dosage may be delivered over two or more inhalations, such as at least 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 inhalations. A dosage may also be delivered over 1 to 100 inhalations, such as 1-3, 1-4, 1-5, 1-6, 1-10, 1-20, 1-50, 1-80, 1-100, 2-5, 2-6, 2-10, 2-20, 2-50, 2-100, 5-10, 5-20, 5-50, 5-100, 10-20, 10-50, 10-100, 20-50, 20-100, or 50-100 inhalations. For example, a 10 mg dosage may be delivered by providing two unit doses of 5 mg each, and the two unit doses may be separately inhaled. In certain embodiments, the overall dose of the at least one anticoagulant or antiplatelet agent ranges from 0.1 mg to 200 mg, such as 0.5 mg to 150 mg, or 1 mg to 100 mg. In some instances the at least one anticoagulant or antiplatelet agent can be administered as-needed titrating the dosage to effect.

The present invention can be directed to a method of self-diagnosing and treating acute coronary syndrome. The method comprises self-administering by inhalation an effective amount of at least one anticoagulant or anti platelet agent within two hours, such as within one hour, 30 minutes, or within 15 minutes, of the self-diagnosing. In some cases, the patient can self-titrate. For example, the patient can self-administer, e.g., by using a nebulizer, until disabling symptoms disappear.

The time for onset of action is also typically short. For instance, the amount of the pharmaceutical composition can peak in the left atrium within 20 minutes of initiating the administering, such as within 15 minutes, within 10 minutes, or within 5 minutes of initiating the administering. In some embodiments, the method of the present invention allows the patient to avoid other therapies.

An effective amount can be that which is effective to reduce clotting in ischemic events, clotting, angina, myocardial infarction, or stroke, when the at least one anticoagulant or antiplatelet agent is non-invasively administered, preferably by inhalation, so that the at least one anticoagulant or antiplatelet agent first enters the heart via the left atrium. In the preferred method, the amount of the agent peaks in the left atrium at a time ranging from 30 seconds to 90 minutes, 30 seconds to 60 minutes, or 30 seconds to 30 minutes after initiating the administration.

In some embodiments, the effective amount of the at least one anticoagulant or antiplatelet agent produces a ratio of factor-Xa to factor-IIa activity in the left atrium peaking at a range from 1 to 30, for example, at a range from 1 to 5, from 1 to 10, from 1 to 15, from 1 to 20, from 1 to 25, from 1 to 30, from 3 to 5, from 3 to 10, from 3 to 15, from 3 to 20, from 3 to 25, from 3 to 30, from 5 to 10, from 5 to 15, from 5 to 20, from 5 to 25, from 5 to 30, from 10 to 15, from 10 to 20, from 10 to 25, from 10 to 30, from 15 to 20, from 15 to 25, from 15 to 30, from 20 to 25, from 20 to 30, or from 25 to 30. In one example, effective amount of the at least one anticoagulant or antiplatelet agent produces a ratio of factor-Xa to factor-IIa activity in the left atrium peaking at a range from 3 to 21.

The pharmaceutical composition is selected so that preferably 10% to 80% of the at least one anticoagulant or antiplatelet agent administered can reach the left atrium. In some embodiments, about 10% to 20%, about 10% to 40%, about 10% to 60%, about 10% to 80%, about 20% to 40%, about 20% to 60%, about 20% to 80%, about 40% to 60%, about 40% to 80%, or about 60% to 80% of the at least one anticoagulant or antiplatelet agent administered can reach the left atrium.

An IV drug is immediately available, as it does not have any absorption barriers, while the inhaled drug is dependant on lung deposition and absorption factors before it reaches systemic circulation. An estimated 10-15% of drug in steady state is pumped through the coronary arteries.

An inhaled delivery of the drug can provide five times more drug concentrations in the coronary arteries as a bolus followed by similar concentrations when in steady state. Hence, the PK of an inhaled drug can provide a more effective concentration profile compared to the IV drug. For example, the PK of such a drug is expected to not only reduce the dose but also reduce the frequency of administration.

An evaluation of the pk of Certoparin, a low molecular weight heparin, shows that it is likely to have a sustained pk profile covering 24-48 hours compared to the sub-cutaneous injection. Enoxiparin is a low molecular weight heparin that is indicated for the prevention of ischemia in cardiac conditions such as angina, unstable angina, non Q-wave myocardial infarction. A mathematical model shows that an inhaled medication is expected to exhibit a higher concentration in the arteries compared to venous concentrations (I-5×). This differential permits targeting the left atrium and coronary arteries with high bolus drug. The left atrium is a useful target as clots are formed in this region in AF patients and the coronaries are the right target as the clots are formed in this region in patients diagnosed with unstable angina and myocardial infarction.

V. Device

Figure 2:
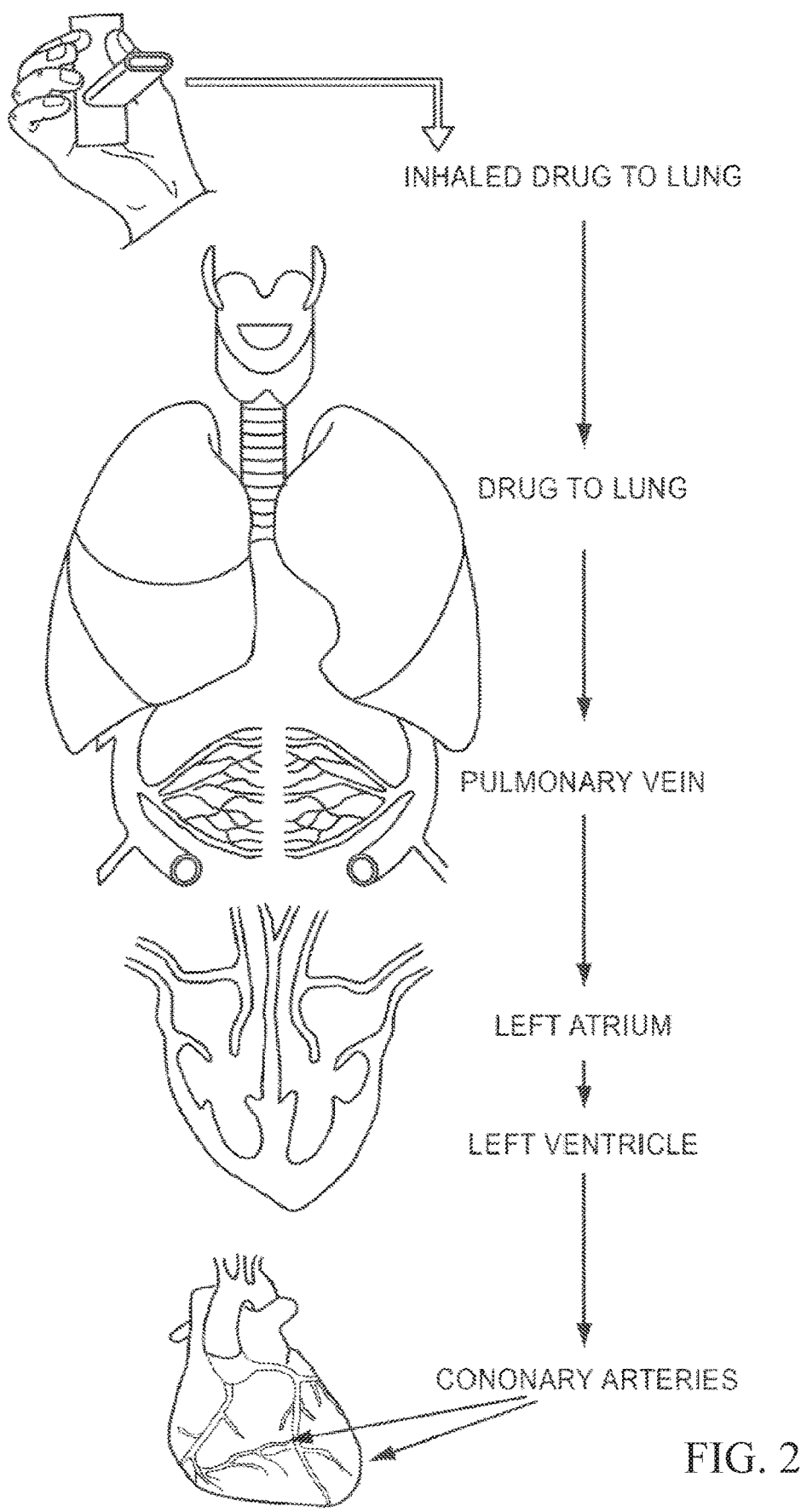
FIG. 2 shows how inhaled drug of the present invention passes through the pulmonary vein to the left atrium.
Figure 3:
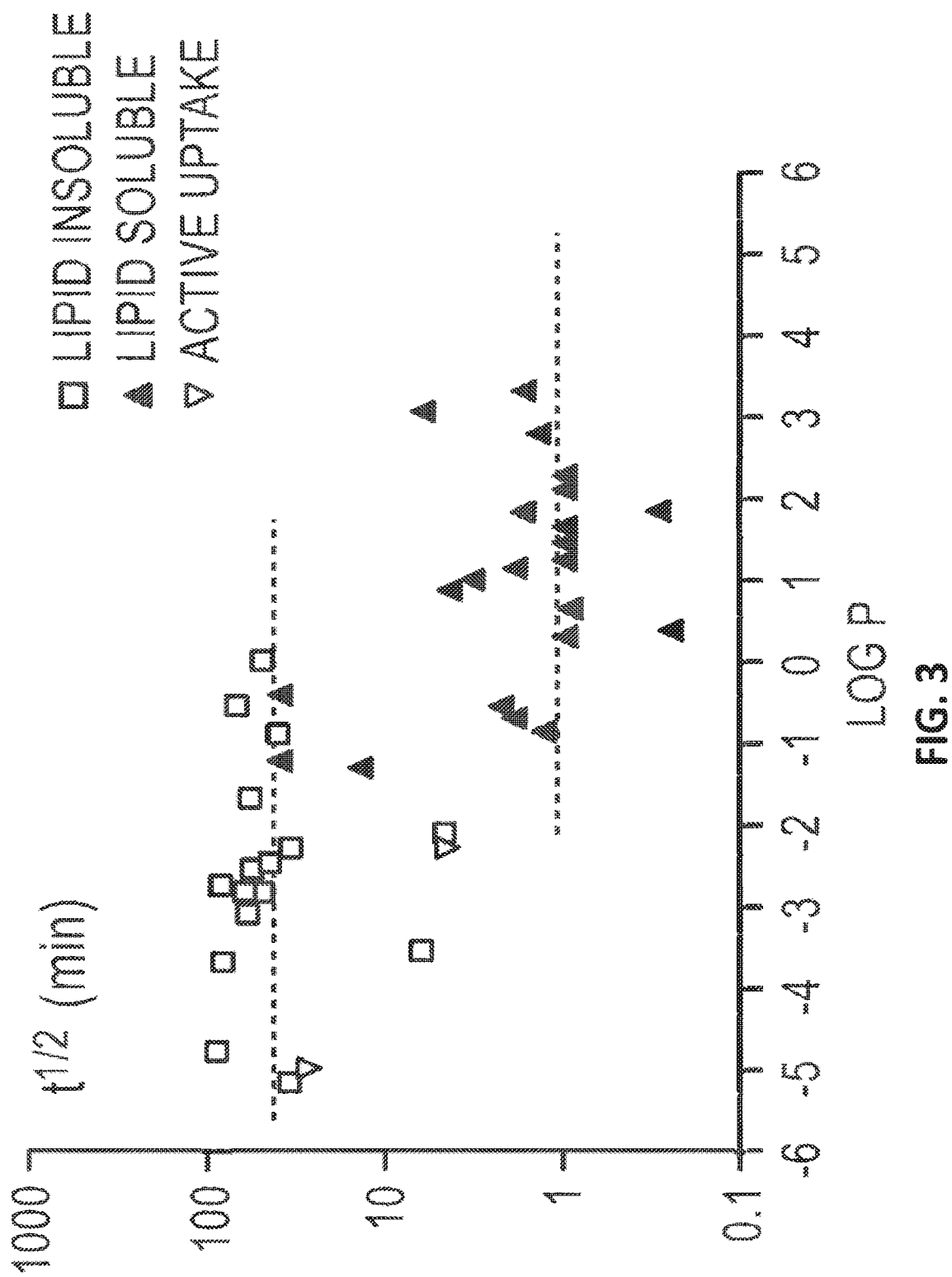
FIG. 3 shows that molecules with high Log-P values and those with high lipid solubility can exhibit faster absorption through the lung.

Inhalation can be one of the shortest routes for a drug to reach the heart, as shown in FIGS. 1 and 2. Drugs delivered by inhalation can generally exhibit "pulsatile pharmacokinetics" of transient high drug concentrations, followed by dilution to sub-therapeutic levels. This characteristic can be expected to reduce much of the dose dependent pro-arrhythmia and QT prolongation seen with both oral and IV therapies. FIG. 3 shows that molecules with high Log-P values and those with high lipid solubility can exhibit faster absorption through the lung.

The pharmaceutical composition may be delivered by a nebulizer as described in WO 99116420, by a metered dose inhaler as described in WO 99116422, by a liquid dose instillation apparatus as described in WO 99116421. Nebulizers impart energy into a liquid pharmaceutical composition to aerosolize the liquid, and to allow delivery to the pulmonary system, e.g., the lungs, of a patient. A nebulizer comprises a liquid delivery system, such as a container having a reservoir that contains a liquid pharmaceutical composition. The liquid pharmaceutical composition generally comprises an active agent that is either in solution or suspended within a liquid medium.

The nebulizer can be a jet nebulizer, a vibrating mesh nebulizer, or an ultrasonic wave nebulizer.

The nebulizer has the ability to rapidly deliver the aerosol at a rate that assures availability of a bolus dose in the heart. The nebulizer can aerosolize the pharmaceutical composition in short amount of time. In some cases, the nebulizer can aerosolize the pharmaceutical composition (e.g. at least 30 mg of flecainide) in less than about 20 minutes, such as less than about 10 seconds, 20 seconds, 30 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. For example, the nebulizer can aerosolize at least 30 mg of flecainide in less than 3 minutes. In some cases, the nebulizer can aerosolize the pharmaceutical composition in about 10 seconds to 20 minutes, such as about 10-20 seconds, 10-30 seconds, 10 seconds to 1 minute, 10 seconds to 2 minutes, 10 seconds to 3 minutes, 20-30 seconds, 20 seconds to 1 minute, 20 seconds to 2 minutes, 20 seconds to 3 minutes, 30 seconds to 1 minute, 30 seconds to 2 minutes, 30 seconds to 3 minutes, 1-2 minutes, 1-5 minutes, 2-20 minutes, 2-10 minutes, 2-5 minutes, 5-20 minutes, 5-10 minutes, or 10-20 minutes. For example, the nebulizer can aerosolize at least 30 mg of flecainide in about 30 seconds to 3 minutes.

One or more embodiments of the present invention may be used in conjunction with liquid dose instillation or LDI techniques as disclosed in, for example, WO 99116421, which is incorporated herein by reference in its entirety. Liquid dose instillation involves the direct administration of a formulation to the lung. With respect to LDI the formulations are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical microdispersion prior to, during or following administration.

The pharmaceutical composition of one or more embodiments of the present invention typically has improved emitted dose efficiency. Accordingly, high doses of the pharmaceutical composition may be delivered using a variety of aerosolization devices and techniques. The emitted dose (ED) of the particles of the present invention may be greater than about 30%, such as greater than about 40%, greater than about 50%, greater than about 60%, or greater than about 70%.

A method comprises administering to free breathing patients by way of an aerosol generator device and/or system for administration of aerosolized medicaments such as those disclosed in U.S. Published Application Nos. 20050235987, 20050211253, 20050211245, 20040035413, and 20040011358, the disclosures of which are incorporated herein by reference in their entireties.

Also disclosed herein is a kit comprising a container comprising the pharmaceutical composition as disclosed herein; and an aerosolization device or inhaler. In some embodiments, the kit further comprises an instruction, for example, an instruction describes the operation of the aerosolization device or inhaler. In some embodiments, the instruction describes the dosage of the pharmaceutical composition. In some embodiments, the kit may further comprise a package, such as a bag or a box, which contains the container and the device (e.g., aerosolization device or inhale).

VI. Example

The following examples are offered to illustrate, but not to limit, the claimed invention.

Example I: Comparison of the Concentrations in the Coronaries for IV and Inhaled Tirofiban and Eptifibatide The lung is the shortest route for drug to the coronary arteries with minimal dilution other than injecting the drug directly into the coronaries, e.g. during a PTCA or PCI procedure or CABG surgery. Drugs delivered via the lung have the quickest onset action compared to those delivered via the oral route. Pulmonary drug delivery to the heart is better than intravenous injection as the drug targets the coronary arteries where it is primarily required as preventative to any ischemic conditions.

Tables 2 and 3 show the concentrations in the coronaries between and IV and inhaled Tirofiban and Eptifibatide.

TABLE 2

Comparison of the Concentrations in the coronaries for IV and inhaled Tirofiban.

|  | IV Drug | Inhaled drug |
|---|---|---|
| Dose | 0.9 to 1.2 mg (administered as bolus at 0.5 µg/kg/min for 30 min; average BW 60-80 kg) | Assume 100% bio-availability Assume IV |
| Drug dilution in blood | 0.18-0.24 µg/ml reaches the heart through the lung | No dilution occurs |
| Drug conc. in coronaries | 0.018 to 0.036 µg in coronaries | 1.62 to 3.03 mg bolus followed by same as IV concentrations |
| Stead state in blood | 0.1 to 0.25 µg/ml | 0.1 to 0.25 µg/ml |

TABLE 3

Comparison of the Concentrations in the coronaries for IV and inhaled eptifibatide.

|  | IV Drug | Inhaled drug |
|---|---|---|
| Dose | 10.8 to 13.5 mg (administered as bolus at 180 µg/kg for 30 min; average BW 60-80 kg) | Assume 50% bio-availability Assume 16.2 to 20.25 |
| Drug dilution in blood | 2.16-2.7/ml µg reaches the heart through the lung | No dilution occurs |
| Drug cone in coronanes | 0.22 to 0.41 µgin coronaries | 1.62 to 3.03 mg bolus followed by same as IV concentrations Significant opportunity to reduce dose via inhalation |

The method takes advantages of bolus drug concentration in the coronary arteries followed by similar to IV steady state concentrations. The existing drugs include small peptides and small molecules and can have a high pulmonary bioavailability and Tmax within 10 mins. Examples include Tirofiban, a small molecule that has low aqueous solubility and high lipid solubility. These characteristics predict the drug is expected to have a high pulmonary bioavailability. Other related molecules are Abciximab and Eptifibatide, a cyclic peptide. Table 4 shows that high lipid soluble molecules (characterized by Log p) are expected to have high pulmonary bioavailability.

TABLE 4

GP IIb/IIIa inhibitors expected to have high Pulmonary BA

| Drug | Lipid solubility | Log P |
|---|---|---|
| Tirofiban | High | 1.4 |
| Eptifibatide | Moderate | −2.3 |

Example 2: Comparison of the Concentrations in the Coronaries for IV and Inhaled Enoxaparin

TABLE 5

Comparison of the Concentrations between IV and inhaled enoxaparin

|  | IV Drug | Inhaled drug |
|---|---|---|
| Dose | 80-100 mg as SC injection depot lasts for 12 hrs | 80-100 mg inhaled (assume same dose) depot lasts for 24 hrs |
| Drug dilution in blood | Diluted in 5000 ml of blood | No dilution occurs |
| Drug Conc. in left atrium |  |  |
| Drug conc. in coronaries | 10% of drug in whole blood | About 10% of drug absorbed reaches coronaries undiluted |

Pulmonary delivery creates a depot in the lung and allows the drug to slowly be absorbed to maintain continuously high concentrations in the left atrium and coronary arteries. The arterial and venous drug concentrations are expected to normalize around 3-12 hrs so there is a high drug concentration exposure in the left atrium and coronary arteries.

Example 3: Evaluation of Efficacy of Anticoagulants

To assess the efficacy of anticoagulants delivered via intratracheal (IT) inhalation, four different anticoagulants were tested in a dog study.

PK as well as biomarkers of blood in the Left Atrium (LA) and Coronary Sinus (CS) were monitored. These locations were chosen as these are the sites whereby clot formation occurs that leads to Myocardial Infarction or results in stroke.

Drugs and Doses Tested

TABLE 6

Comparison of four anticoagulants tested in this study

| Drug | Typical use | IV dose | IT dose |
|---|---|---|---|
| Bivalirudin | First line in PCI/PCT. | 2 mg/Kg | 2 mg/Kg 8 mg/Kg |
| Argatroban | used as first line in HIT (Heparin induced thrombocytopenia) patients - patients who are sensitive to heparin. | 3 mg | 5 mg |
| LMWH (Lovenox) | Used as sub-q in treating DVT, but has a much more predictable pk than unfractionated heparin. | Not tested as it is widely reported in the literature | 2 mg/Kg |

TABLE 6-continued

Comparison of four anticoagulants tested in this study

| Drug | Typical use | IV dose | IT dose |
|---|---|---|---|
| Heparin | First line in CABG. | Not tested as it is widely reported in the literature | 5000 units/kg |

These drugs and doses were selected to represent a wide spectrum of anticoagulant classes. One anticoagulant was tested in one dog on each arm of this study.

Assays to Evaluate of the Efficacy of Anticoagulants

The standard laboratory tests commonly used to evaluate the efficacy of anticoagulants are the following:

Activated clotting time (ACT), measures the time in seconds needed for whole blood to clot upon exposure to an activator of an intrinsic pathway by the addition of such as factor XII activators.

Factor Xa inhibition; Prothrombin Time (PT): measures the integrity of the extrinsic system as well as factors common to both systems; and Activated Partial Thromboplastin Time (aPTT or PTT): measures the integrity of the intrinsic system and the common components and factor-Xa inhibition.

The first test, ACT, was the key in the management of ACS. The latter three tests provided information regarding the prevention of clot formation and growth of an existing clot. The table below summarizes the measurements performed for each anticoagulant in the study.

TABLE 7

Summary of the measurements performed for each anticoagulant in the study.

| Drug | ACT | Factor Xa Inhibition | PT | PTT |
|---|---|---|---|---|
| Bivalirudin | X | | X | X |
| Argatroban | X | | X | X |
| LMWH (Lovenox) | X | X | | |
| Heparin | X | X | | |

Measurements were performed in the blood collected from Left Atrium (LA) and in the Coronary sinus (CS)—the targets for stroke prevention and Myocardial Infarction (MI), respectively.

Blood samples were drawn at baseline, and at 1, 3, 5, 10, 15, 60 minutes after initiating the administration of the anticoagulant, and then every hour up to 3 hours based on readings and half life of the specific anticoagulant.

Results

TABLE 8

Comparison of the results after initiating the IV and IT administrations of Bivalirudin.

| Timepoint (min) | ACT LA (sec) | PT LA (sec) | PTT LA (sec) | PTCS (sec) | PTTCS (sec) |
|---|---|---|---|---|---|
| IV Bivalirudin 2 mg/kg ||||||
| 0 | 106 | 5.8 | 9.7 | 5.8 | 10.6 |
| 1 | 242 | 34.6 | 42.4 | | |
| 3 | 214 | 28.8 | 36 | 25 | 35.1 |
| 5 | 203 | 20.8 | 26.3 | | |
| 10 | 174 | 17.4 | 23.8 | | |
| 15 | 168 | 12.1 | 19.1 | 17.2 | 120 |
| 30 | 135 | 7.6 | 15.7 | | |
| 60 | 106 | 6.4 | 11 | 6 | 120 |
| IT Bivalirudin 2 mg/kg ||||||
| 0 | 90 | 6.1 | 8.4 | 6.75 | 8.4 |
| 1 | 95 | 6 | 8.3 | | |
| 3 | 95 | 5.4 | 9.1 | 5.45 | 120 |
| 5 | 101 | 5.8 | 8.8 | | |
| 10 | 101 | 6.2 | 11.5 | | |
| 15 | 95 | 5.7 | 9.4 | 9.3 | 120 |
| 30 | 95 | 5.8 | 8.2 | | |
| 60 | 95 | 7.2 | 11.9 | 6.3 | 10.7 |
| IT Bivalirudin 8 mg/kg ||||||
| 0 | 78 | 6.4 | 10.3 | 6.5 | 12.5 |
| 1 | 95 | 6.1 | 8.4 | | |
| 3 | 89 | 6.9 | 11.9 | 5.5 | 8.1 |
| 5 | 90 | 6.3 | 11.3 | | |
| 10 | 89 | 7 | 9.5 | | |
| 15 | 90 | 6.7 | 9.6 | 7 | 120 |
| 30 | 90 | 6.6 | 9.9 | | |
| 60 | 89 | 5.9 | 13 | 5.5 | 21.3 |

Specific Observations of Bivalirudin:

IV prolonged the ACT, PT and aPTT; and IT had NO effect on any of the coagulation tests—ACT, PT or aPTT— No change to base line at both the 2 mg/kg and 8 mg/kg indicating that either Bivalirudin was stuck in the lung or metabolized, since Bivalirudin was engineered as a peptide to have short half-life of 1-2 hrs.

TABLE 9

Comparison of the results after initiating IV and IT administrations of Argatroban.

| Timepoint | ACT LA (sec) | PT LA (sec) | PTT LA (sec) | PT CS (sec | PTT CS (sec) |
|---|---|---|---|---|---|
| IV Argatroban 3 mg ||||||
| 0 | 101 | 9.1 | 48.2 | 6.5 | 20.9 |
| 1 | 535 | 44.3 | 41.5 | | |
| 3 | 1000 | 36.3 | 29.5 | 33.7 | 20 |
| 5 | 489 | 30.1 | 23.4 | | |
| 10 | 326 | 22 | 20.9 | | |
| 15 | 264 | 18 | 25.1 | 20.2 | 33.8 |
| 30 | 185 | 11.5 | 12.2 | | |
| 60 | 140 | 7.9 | 9.8 | 8.6 | 24.9 |
| 120 | 107 | 6.7 | 49.3 | | |
| T Argatroban 5 mg ||||||
| Timepoint | ACT LA (sec) | PT LA (sec) | PTT LA (sec) | PTCS (sec | PTT CS (sec) |
| 0 | 84 | 6.3 | 13.3 | 6.5 | 16.1 |
| 1 | 89 | 6.7 | 12.5 | | |

TABLE 9-continued

Comparison of the results after initiating
IV and IT administrations of Argatroban.

| 3 | 73 | 7 | 17.7 | 6.8 | 18.4 |
| 5 | 106 | 7.2 | 17.2 | | |
| 10 | 135 | 8.6 | 20.1 | | |
| 15 | 180 | 10.4 | 17.8 | 8.9 | 9.5 |
| 30 | 259 | 12 | 13.2 | | |
| 60 | 180 | 8.1 | 11.1 | 8.6 | 40.3 |
| 120 | 129 | 7.3 | 10.4 | | |

Specific Observations of Argatroban:

IV prolonged the ACT, PT and aPTT; IT prolonged the ACT in about 15-30 mins; and IT showed very marginal spikes in PT and aPTT.

TABLE 10

The results after initiating IT administration of LMWH.
IT LMWH 2 mg/kg

| Time-point | ACT LA (sec) | Xa LA | Xa CS |
|---|---|---|---|
| 0 | 90 | 0.16 | 0.14 |
| 1 | 107 | 0.30 | |
| 3 | 95 | 0.23 | 0.20 |
| 5 | 101 | 0.28 | |
| 10 | 101 | 0.37 | |
| 15 | 101 | 0.46 | 0.38 |
| 30 | 95 | 0.60 | |
| 60 | 101 | 0.71 | 0.68 |
| 120 | 95 | 0.66 | |
| 180 | 95 | 0.67 | |

Specific Observations of LMWH:

IT had NO effect on ACT as expected; IT had a significant and steady inhibition of Factor Xa in both Left Atrial as well as Coronary Sinus—indicating that LMWH could be used in different doses for both MI and stroke prevention. The inhibition was prolonged and was steady at 180 mins.

TABLE 11

The results after initiating IT administration of heparin.
IT Heparin 5000 units/kg

| Time-point | ACT LA (sec) | Xa LA HEP | LA ProtC | XaCS HEP | CS ProtC |
|---|---|---|---|---|---|
| 0 | 106 | 0.010 | 105 | 0.0 | 101 |
| 1 | 95 | 0.020 | | | |
| 3 | 90 | 0.020 | 112 | 0.0 | 101 |

TABLE 11-continued

The results after initiating IT administration of heparin.
IT Heparin 5000 units/kg

| Time-point | ACT LA (sec) | Xa LA HEP | LA ProtC | XaCS HEP | CS ProtC |
|---|---|---|---|---|---|
| 5 | 90 | 0.010 | | | |
| 10 | 95 | 0.010 | | | |
| 15 | 95 | 0.010 | 117 | 0.0 | 102 |
| 30 | 89 | 0.030 | | | |
| 60 | 90 | 0.020 | 115 | 0.0 | 117 |
| 120 | 90 | 0.050 | 114 | | |
| 180 | 95 | 0.070 | | | |

Specific Observations of Heparin:

IT had NO effect on ACT and NO immediate effect on factor Xa assay.

Discussion

Based on the data above, the following observations were made:

There was no prolongation of ACT observed with IT bivalirudin, heparin and LMWH. IT Argatroban increased and prolonged ACT by as much as 3.2-fold above baseline. The bivalirudin may be metabolized in the lung as this molecule, related to hirudin, was specifically engineered to be metabolized quickly to address bleeding complications seen in hirudin. Bivalirudin has a 2-4 hours half-life. Thus, it is possible that the systemic blood (post lung) "hardly sees" any parent bivalirudin—similar effect has been observed with adenosine. Argatroban prolonged the ACT and the ACT returns to base line in 2 hours.

TABLE 12

Summary of the anticoagulants tested in the study

| Bivalirudin | Argatroban | LMWH (Lovenox) | Unfractionated Heparin |
|---|---|---|---|
| | Direct Thrombin Inhibitor | | Factor Xa inhibitor |
| Inhaled bivalirudin showed NO effect | Inhaled argatroban showed increased and prolonged ACT in LA and CS, whereas the increases in PT and aPTT were minimal | Factor Xa increased and prolonged in both LA and CS and stay extended beyond 180 mms | No prolongation of tested biomarker |
| Possibly metabolized in lungs | Dose and formulation related but encouraging for MI | Potential for a good stroke prevention strategy | |
| | IV control exhibited expected increases in ACT, PT and aPTT | | IV control not tested as highly published |

Example 4: Use of Inhaled Anticoagulant for Treatment of Myocardial Infarction (Ail)

Inhaled anticoagulant (e.g. Argatroban) will be administered (e.g., self-administered) to a patient suffering a Myocardial Infarction (MI) early to ensure that the patient is in an anti-coagulated state by the time the patient arrives at the hospital or point of care. This will facilitate further interventions, for which an anti-coagulated state is important. In this example, a dose of 0.1 to 150 mg/kg can be sufficient to achieve an anti-coagulated state in 30 minutes.

The short half-life of the Argatroban and its localized effect have an additional advantage: if it is later determined that the patient was not in MI but in a different condition, the patient will return to a normal coagulation state in 3 hours after initiating the administration of the anticoagulant.

Example 5: Use of Inhaled Anticoagulant for Prevention of Stroke

A periodic dose of inhaled anticoagulant (e.g. LMWH) of 0.1 to 150 mg/kg will be used in patients undergoing atrial fibrillation (AFIB) episodes to target the Atrial Appendix to ensure that no blood clots will be formed, thus preventing a stroke. The periodic dose will be administered twice daily, daily, every other day, weekly, monthly

Example 6: Use of Inhaled Anticoagulant in Patients Needing Heart Valve Replacement Inhaled anticoagulant (e.g. Argatroban) will be administered to a patient undergoing heart valve replacement to target the heart to reach an anti-coagulated state. In this example, a dose of 0.1 to 150 mg/kg can be sufficient to achieve an anti-coagulated state in 30 minutes.

The short half-life of the Argatroban and its localized effect have an additional advantage that once the procedure is completed, the patient will return to a normal coagulation state in 3 hours after initiating the administration of the anticoagulant.

Example 7: Use of Inhaled Anticoagulant in Patients with Severe Coronary Heart Disease but not Eligible for CABG Inhaled anticoagulant (e.g. Argatroban) will be administered to a patient to restore normal blood flow in partially obstructed coronary artery. This will be of particular advantage for patients that are for some reason ineligible for CABG surgery. In this example, a dose of 0.1 to 150 mg/kg can be sufficient to achieve an anti-coagulated state in 30 minutes, while the rest of the body remains in a normal coagulation state.

Example 8: Use of Inhaled Anticoagulant in Heart Transplant Patients

Inhaled anticoagulant (e.g. Argatroban) will be administered to a patient undergoing heart transplant to target the heart to reach an anti-coagulated state. In this example, a dose of 0.1 to 150 mg/kg can be sufficient to achieve an anti-coagulated state in 30 minutes.

The short half-life of the Argatroban and its localized effect have an additional advantage that once the procedure is completed, the patient will return to a normal coagulation state in 3 hours after initiating the administration of the anticoagulant.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treatment of acute coronary syndrome and/or thrombosis comprising:

administering, by inhalation, an effective amount of a pharmaceutical composition to a subject in need thereof, wherein the pharmaceutical composition comprises (a) a univalent direct thrombin inhibitor selected from the group consisting of argatroban, melagatran, ximelagatran, and dabigatran, wherein at least about 5% of the univalent direct thrombin inhibitor is delivered to the coronary arteries.

2. The method of claim 1, wherein the pharmaceutical composition further comprises a direct factor Xa inhibitor.

3. The method of claim 1, wherein the pharmaceutical composition is administered by a condensation aerosol, a liquid nebulizer, a nebulizer, an active dry powder inhaler, a passive dry powder inhaler, or a metered dose inhaler.

4. The method of claim 1, wherein the pharmaceutical composition is in the form of an aerosol, a dry powder, or nebulized droplets.

5. The method of claim 1, wherein the pharmaceutical composition has a mass median aerodynamic diameter of less than about 10 μm.

6. The method of claim 1, wherein the pharmaceutical composition is self-administered by the patient.

7. The method of claim 1, wherein the effective amount is administered in between about 1 and about 10 inhalations.

8. The method of claim 1 wherein the acute coronary syndrome comprises ischemic events, clotting, angina, myocardial infarction, or any combination thereof.

9. The method of claim 1, wherein the effective amount is between about 0.1 and 150 mg/kg.

10. The method of claim 2, wherein the direct factor Xa inhibitor is at least one of rivaroxaban, apixaban, edoxaban, betrixaban, darexaban, TAK-442 (letaxaban), eribaxaban, or otamixaban.

11. A method for prevention of acute coronary syndrome and/or thrombosis in a patient comprising:

inhaling an effective amount of a pharmaceutical composition, the pharmaceutical composition comprising an antithrombotic compound, wherein the antithrombotic compound comprises (a) a univalent direct thrombin inhibitor selected from the group consisting of argatroban, melagatran, ximelagatran, and dabigatran, wherein at least about 5% of the univalent direct thrombin inhibitor is delivered to the coronary arteries and/or wherein about 10% to about 80% of the antithrombotic compound is delivered to the left atrium.

12. The method of claim 11, wherein the administration prevents platelet aggregation.

13. The method of claim 11, wherein the patient is suffering from at least one of stable angina, unstable angina, myocardial infarction, valvular heart disease, stroke, and atrial fibrillation.

14. The method of claim 11, wherein the patient is a heart transplant or heart valve replacement patient.

15. The method of claim 11, wherein the pharmaceutical composition further comprises a pharmaceutically acceptable excipient.

16. The method of claim 11, wherein the pharmaceutical composition is delivered at a therapeutic level to the heart and coronary arteries and at a sub-therapeutic level to rest of the body other than the heart and coronary arteries.

17. The method of claim 11, wherein the pharmaceutical composition further comprises a direct factor Xa inhibitor.

18. The method of claim 17, wherein the direct factor Xa inhibitor is at least one of rivaroxaban, apixaban, edoxaban, betrixaban, darexaban, TAK-442 (letaxaban), eribaxaban, or otamixaban.

* * * * *